US010093757B2

(12) United States Patent
Weissenbach et al.

(10) Patent No.: US 10,093,757 B2
(45) Date of Patent: Oct. 9, 2018

(54) SILANOL CONDENSATION CATALYSTS FOR THE CROSS-LINKING OF FILLED AND UNFILLED POLYMER COMPOUNDS

(71) Applicant: Evonik Degussa GmbH, Essen (DE)

(72) Inventors: Kerstin Weissenbach, Bridgewater, NJ (US); Aristidis Ioannidis, Rheinfelden (DE); Bastian Bielawski, Rheinfelden (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 13/903,594

(22) Filed: May 28, 2013

(65) Prior Publication Data

US 2013/0253144 A1 Sep. 26, 2013

Related U.S. Application Data

(62) Division of application No. 13/059,546, filed as application No. PCT/EP2009/058721 on Jul. 9, 2009.

(30) Foreign Application Priority Data

Sep. 9, 2008 (DE) .................. 10 2008 041 918

(51) Int. Cl.
| | | |
|---|---|---|
| *C08F 110/02* | (2006.01) | |
| *C07F 7/18* | (2006.01) | |
| *C08F 230/08* | (2006.01) | |
| *C08K 5/5419* | (2006.01) | |

(52) U.S. Cl.
CPC .......... *C08F 110/02* (2013.01); *C07F 7/1896* (2013.01); *C08F 230/08* (2013.01); *C08K 5/5419* (2013.01)

(58) Field of Classification Search
CPC .................................. C08K 5/5425
USPC .................................. 252/182.14; 525/333.7
See application file for complete search history.

(56) References Cited

U.S. PATENT DOCUMENTS

| | | | | |
|---|---|---|---|---|
| 2,654,722 | A * | 10/1953 | Young ...................... | C08K 5/20 106/169.47 |
| 3,869,308 | A | 3/1975 | Graham | |
| 5,282,998 | A | 2/1994 | Horn et al. | |
| 5,885,341 | A | 3/1999 | Standke et al. | |
| 6,232,376 | B1 * | 5/2001 | Tsukada et al. ................. | 524/99 |
| 6,448,343 | B1 * | 9/2002 | Schombourg et al. ....... | 525/288 |
| 6,528,585 | B1 | 3/2003 | Standke et al. | |
| 6,767,982 | B2 | 6/2004 | Standke et al. | |
| 6,780,955 | B2 | 8/2004 | Barfurth et al. | |
| 6,864,323 | B2 | 3/2005 | Schlosser et al. | |
| 6,890,981 | B1 * | 5/2005 | Luginsland ................... | 524/262 |
| 7,250,156 | B2 | 7/2007 | Vernaire et al. | |
| 7,781,520 | B2 | 8/2010 | Standke et al. | |
| 8,236,918 | B2 | 8/2012 | Mueh et al. | |
| 8,431,646 | B2 | 4/2013 | Giessler-Blank et al. | |
| 2002/0147300 | A1 * | 10/2002 | Matsumoto .............. | B41N 3/08 528/422 |
| 2003/0083409 | A1 * | 5/2003 | Bienmuller et al. ......... | 524/127 |
| 2003/0114604 | A1 | 6/2003 | Schlosser et al. | |
| 2003/0134969 | A1 | 7/2003 | Schlosser et al. | |
| 2003/0171471 | A1 * | 9/2003 | Pritschins ............... | B29C 33/60 524/306 |
| 2003/0203019 | A1 * | 10/2003 | Cornelius et al. ............ | 424/465 |
| 2005/0147630 | A1 | 7/2005 | Hasegawa et al. | |
| 2006/0122296 | A1 * | 6/2006 | Prud'homme et al. ....... | 524/265 |
| 2006/0167206 | A1 | 7/2006 | Maier et al. | |
| 2006/0198802 | A1 * | 9/2006 | Ito et al. ......................... | 424/62 |
| 2006/0235156 | A1 * | 10/2006 | Griswold et al. ............. | 525/192 |
| 2007/0207229 | A1 * | 9/2007 | Aoki ............................. | 424/774 |
| 2007/0260018 | A1 * | 11/2007 | Phillips, Jr. .............. | C08K 5/01 525/329.1 |
| 2008/0038549 | A1 * | 2/2008 | Griswold et al. ............. | 428/343 |
| 2008/0039576 | A1 * | 2/2008 | Griswold et al. ............. | 524/502 |
| 2008/0187673 | A1 | 8/2008 | Standke et al. | |
| 2008/0193397 | A1 | 8/2008 | Kroll et al. | |
| 2009/0005518 | A1 | 1/2009 | Just et al. | |
| 2009/0247712 | A1 * | 10/2009 | Tanaka et al. ................ | 525/451 |
| 2011/0144277 | A1 | 6/2011 | Weissenbach et al. | |
| 2011/0144278 | A1 | 6/2011 | Weissenbach et al. | |
| 2011/0282024 | A1 | 11/2011 | Weissenbach et al. | |
| 2012/0080637 | A1 | 4/2012 | Herzog et al. | |
| 2012/0328760 | A1 * | 12/2012 | Harada .................... | A23D 7/00 426/590 |

FOREIGN PATENT DOCUMENTS

| | | |
|---|---|---|
| DE | 198 48 351 | 4/2000 |
| EP | 1 288 235 | 3/2003 |
| EP | 1 318 526 | 6/2003 |
| WO | WO 2006/081892 | 8/2006 |
| WO | WO 2008053875 A1 * | 5/2008 |

OTHER PUBLICATIONS

International Search Report dated Jan. 18, 2010 in PCT/EP09/58721 filed Jul. 9, 2009.
International Search Report dated Jan. 18, 2010 in Patent Application No. PCT/EP2009/058721 with English Translation of Category of Cited Documents.
U.S. Appl. No. 11/572,555, filed Jan. 23, 2007, US 2009/0005518 A1, Just, et al.
U.S. Appl. No. 13/059,546, filed Feb. 17, 2011, US2011/0144278 A1, Weissenbach, et al.
U.S. Appl. No. 14/360,120, filed May 22, 2014, Standke, et al.
U.S. Appl. No. 14/360,114, filed May 22, 2014, Standke, et al.
U.S. Appl. No. 14/360,127, filed May 22, 2014, Standke, et al.

\* cited by examiner

*Primary Examiner* — Michael M Dollinger
(74) *Attorney, Agent, or Firm* — Grüneberg and Myers PLLC

(57) ABSTRACT

The invention relates to a composition of an organofunctional silane compound, particularly of a mono-unsaturated silane compound, and of an organic acid or a precursor compound which releases said organic acid, and to a method for the production of polymer compounds such as granulates and/or finished products from thermoplastic base polymers and/or monomers and/or prepolymers of the thermoplastic base polymer utilizing the composition, the organic acid, or the precursor compound which releases said organic acid. The invention also relates to the produced polymers, filled plastics such as, for example, granulates, finished products, molded bodies and/or articles such as pipes or cables. In addition, the invention relates to a kit containing the composition.

14 Claims, No Drawings

SILANOL CONDENSATION CATALYSTS FOR THE CROSS-LINKING OF FILLED AND UNFILLED POLYMER COMPOUNDS

This application is a Divisional of U.S. application Ser. No. 13/059,546, filed on Feb. 17, 2011, pending, which is a National Stage of PCT/EP2009/058721, filed Jul. 9, 2009.

FIELD OF THE INVENTION

The invention relates to a composition of an organofunctional silane compound, in particular of a monounsaturated silane compound, and of an organic acid, or of a precursor compound that liberates an acid, and in particular relates to an olefinic silicon-containing precursor compound of an organic acid, and also to processes for producing compounded polymer materials, such as granules and/or finished products, made of thermoplastic parent polymers, and/or monomers, and/or prepolymer of the thermoplastic parent polymers, with use of the composition, of the organic acid, or of the precursor compound that liberates said acid. The invention further relates to the polymers produced, to filled plastics, for example in the form of granules, finished product, moldings, and/or items such as pipes or cables. A kit comprising the composition is also disclosed.

DISCUSSION OF THE BACKGROUND

It is known that filled and unfilled compounded polymer materials, in particular polyethylene (PE) and copolymers thereof, can be produced by using organotin compounds or aromatic sulfonic acids (Borealis Ambicat®) as silanol condensation catalysts for the crosslinking of silane-grafted or silane-copolymerized polyethylenes. A disadvantage of the organotin compounds is their significant toxicity, while the sulfonic acids are notable for their pungent odor, which continues through all stages of the process into the final product. The compounded polymer materials crosslinked by sulfonic acids are generally not suitable for use in the food-and-drinks sector or in the drinking-water-supply sector, for example for production of drinking-water pipes, because of reaction byproducts. Dibutyltin dilaurate (DBTDL) and dioctyltin dilaurate (DOTL) are conventional tin-based silanol condensation catalysts, and act as catalyst by way of their coordination sphere.

It is known that moisture-crosslinkable polymers can be produced by grafting silanes onto polymer chains in the presence of free-radical generators, where moisture-crosslinking is carried out in the presence of the abovementioned silane hydrolysis catalysts and/or silanol condensation catalysts, after the shaping process. Moisture-crosslinking of polymers using hydrolyzable unsaturated silanes is practiced worldwide for the production of cables, pipes, foams, etc. Processes of this type are known as the sioplas process (DE 19 63 571 C3, DE 21 51 270 C3, U.S. Pat. No. 3,646,155) and the monosil process (DE 25 54 525 C3, U.S. Pat. No. 4,117,195). Whereas the monosil process adds the crosslinking catalyst before the first step of processing is complete, the sioplas process delays addition of the crosslinking catalyst to the subsequent step. Another possibility is to copolymerize vinyl-functional silanes together with the monomers and/or prepolymers directly to give the parent polymer, or to couple these subsequently by way of grafting onto the polymer chains.

EP 207 627 discloses further tin-containing catalyst systems and, with these, modified copolymers based on the reaction of dibutyltin oxide with ethylene-acrylic acid copolymers. JP 58013613 uses Sn(acetyl)$_2$ as catalyst, and JP 05162237 teaches the use of carboxylates of tin, of zinc, or of cobalt together with hydrocarbon groups as silanol condensation catalysts, e.g. dioctyltin maleate, monobutyltin oxide, dimethyloxybutyltin, or dibutyltin diacetate. JP 3656545 uses zinc and aluminum soaps for crosslinking, examples being zinc octylate and aluminum laurate. JP 1042509 likewise discloses the use of organic tin compounds for the crosslinking of silanes, but also discloses alkyl titanic esters based on titanium chelate compounds. JP09-040713 discloses the production of silane-modified polyolefins by reacting a polyolefin and two modified silane compounds with use of an organic acid as silanol condensation catalyst.

It is an object of the present invention to develop novel silane hydrolysis catalysts and/or silanol condensation catalysts which do not have the abovementioned disadvantages of the known catalysts from the prior art, and which can preferably undergo a homogenization process or dispersion process with silane-grafted, and/or silane-copolymerized polymers, and/or monomers, or prepolymers. It is preferable that the silane hydrolysis catalysts and/or silanol condensation catalysts are waxy to solid, and/or have been applied to a carrier material.

SUMMARY OF THE INVENTION

The object is achieved via the composition of the invention, corresponding to the features of Embodiment 1, the masterkit as claimed in Embodiment 9, and the processes of the invention with the features of Embodiment 10 and 11, and also by using the products of the invention, e.g. polymers, compounded polymer materials, products, and the polymer kit corresponding to the features of Embodiments 13, 14, and 15, and also by the use as in Embodiment 16.
Embodiments:

1. A composition
   characterized in that
   it comprises a) at least one silicon-containing precursor compound of an organic acid, and/or one organofunctional silane compound,
   and, if appropriate,
   b) one organic acid, and/or one silicon-free precursor compound containing an organic acid.
2. The composition of Embodiment 1,
   characterized in
   that, in a), at least one
   i) silicon-containing precursor compound of an organic acid corresponds to the general formula I and/or II $$(A)_z SiR^2_x (OR^1)_{4-z-x} \qquad (I)$$

$$(R^1O)_{3-y-u}(R^2)_u(A)_y Si\text{-}A\text{-}Si(A)_y(R^2)_2(OR^1)_{3-y-u} \qquad (II)$$

where, mutually independently, z is 0, 1, 2, or 3, x is 0, 1, 2, or 3, y is 0, 1, 2, or 3, and u is 0, 1, 2, or 3, with the proviso that in formula I z+x is smaller than or equal to (≤)3, and in formula II y+u is independently smaller than or equal to (≤) 2, A is mutually independently in formula I and/or II a monovalent olefin group, and A in the form of a divalent moiety in formula II is a divalent olefin group, $R^1$ corresponds, mutually independently, to a carbonyl-$R^3$group, where $R^3$ corresponds to a hydrocarbon moiety, having from 1 to 45 carbon atoms, and $R^2$ corresponds, mutually independently, to a hydrocarbon group, and/or ii) the organofunctional silane compound corresponds to an unsaturated alkoxysilane, in particular of the general formula III

(III)

where, mutually independently, b is 0, 1, 2, and 3, and a is 0, 1, 2, or 3, with the proviso that in formula III b+a is smaller than or equal to (≤) 3,
where B, mutually independently, is a monovalent $(R^7)_2$C=C($R^7$)-$E_q$-group in formula III, in which $R^7$ are identical or different, and $R^7$ is a hydrogen atom or a methyl group or a phenyl group, the group E is a group from —$CH_2$-, —$(CH_2)_2$-, —$(CH_2)_3$-, —O(O)C$(CH_2)_3$-, or —C(O)O—$(CH_2)_3$-, q is 0 or 1, or isoprenyl, hexenyl, cyclohexenyl, terpenyl, squalanyl, squalenyl, polyterpenyl, betulaprenoxy, cis/transpolyisoprenyl, or corresponds to an $R^6$-$D_p$-[C($R^6$)=C($R^6$)—C($R^6$)=C($R^6$)]$_t$-$D_p$-group, in which $R^6$ are identical or different, and $R^6$ is a hydrogen atom or an alkyl group having from 1 to 3 carbon atoms, or an aryl group, or an aralkyl group, preferably a methyl group of a phenyl group, groups D are identical or different, and D is a group from —$CH_2$-, —$(CH_2)_2$-, —$(CH_2)_3$-, —O(O)C$(CH_2)_3$-, or —C(O)O—$(CH_2)_3$-, and p is 0 or 1, and t is 1 or 2,
$R^5$ is, mutually independently, methyl, ethyl, n-propyl, and/or isopropyl,
$R^4$ is, mutually independently, a substituted or unsubstituted hydrocarbon group.

3. The composition of Embodiment 1 or 2, characterized in
   that, in b), at least one organic acid comprises
   iii.a) a saturated and/or unsaturated fatty acid, and/or a natural or
   synthetic amino acid, and/or as
   iii.b) an acid-contained silicon-free precursor compound, an anhydride or an ester, in particular a natural or synthetic triglyceride and/or phosphoglyceride.

4. The composition of any of Embodiment 1 to 3, characterized in
   that the composition comprises, as component c), at least one free-radical generator.

5. The composition of Embodiment 4, characterized in
   that the free-radical generator is an organic peroxide and/or an organic perester, in particular tert-butyl peroxypivalate, tert-butyl 2-ethylperoxyhexanoate, dicumyl peroxide, di-tert-butyl peroxide, and/or tert-butyl cumyl peroxide, 1,3-di(2-tert-butylperoxyisopropyl)benzene, 2,5-dimethyl-2,5-bis(tert-butylperoxy)hex-3-yne, di-tert-amyl peroxide, 1,3,5-tris(2-tert-butylperoxyisopropyl)benzene, 1-phenyl-1-tert-butylperoxyphthalide, alpha,alpha'-bis(tert-butylperoxy)diisopropylbenzene, 2,5-dimethyl-2,5-di-tert-butylperoxyhexane, 1,1-di(tert-butylperoxy)-3,3,5-trimethylcyclohexane, n-butyl 4,4-di(tert-butylperoxy)valerate, ethyl (3,3-di(tert-butylperoxy)butyrate, 3,3,6,9,9-hexamethyl-1,2,4,5-tetraoxacyclononane, or a mixture of at least two free-radical generators.

6. The composition of any of Embodiments 1 to 5, characterized in
   that the composition comprises, as component d), a stabilizer and/or further added substances and/or mixtures of theses.

7. The composition of any of Embodiments 1 to 6, characterized in
   that the composition comprises, as component e), a thermoplastic parent polymer, a silane-grafted parent polymer, or a silane-copolymerized parent polymer, and/or a monomer and/or prepolymer of said parent polymers, and/or a mixture of these.

8. The composition of any of Embodiments 1 to 7, characterized in
   that the silicon-containing precursor compound of an organic acid is in a form that is liquid, waxy, solid, or bound on a carrier material, and/or the organofunctional silane compound is in a form that is liquid, highly, viscous, waxy, solid, or bound on a carrier material.

9. A masterkit, in particular comprising a composition of any of Embodiments 1 to 8, characterized in
   that it comprises, as component A, from 0.1 to 10% by weight, in component A, of at least one silicon-containing precursor compound of an organic acid, in particular of the general formula I and/or II as defined above, or at least one organic acid, or one silicon-free precursor compound containing organic acid and, making up 100% by weight of component A, one carrier material, one stabilized, one added substance, or mixture of these, and
   if appropriate, as component B, for 60 to 99.9% by weight, in component B, or an organofuncational silane compound of the formula III, where the definitions of b, a, B, $R^4$ and $R^5$ are as above, and also, if appropriate, from 0.05 to 10% by weight of a free-radical generator and, if appropriate, from 0.05 to 10% by weight of at least one stabilizer, and/or from 0.05 to 99.99% by weight of at least one carrier material, stabilizer, added substance, or a mixture of these, where the quantitative data give a total of 100% by weight in component B.

10. A process for producing compounded polymer materials, by
    1) reacting a mixture made of thermoplastic parent polymer with a) at least one silicon-containing precursor compound of an organic acid and/or one organofuncational silane compound and, if appropriate, b) an organic acid, a silicon-free precursor compound containing an organic acid, and also a free-radical generator, in a compounding apparatus, or
    2) reacting a mixture made of thermoplastic parent polymer, in a first step, with a) an organofunctional silane compound, and also a free-radical generator, and shaping the material in a subsequent step, with addition of at least one silicon-containing precursor compound of an organic acid, one silicon-free precursor compound containing an organic acid, and/or one organic acid, and crosslinking the material with exposure to moisture, or
    3) reacting a mixture made of thermoplastic parent polymer in a first step with a) at least one olefinic silicon-containing precursor compound of an organic acid, in particular of the general formulae I and/or II, where z=1, 2, or 3, and also a free-radical generator, and shaping the material in a subsequent step, with addition of at least one silicon-containing precursor of an organic acid, one silicon-free precursor compound containing an organic acid, and/or one organic acid, and crosslinking the material with exposure to moisture, or 4) reacting a mixture made of monomer and/or prepolymer of the thermoplastic parent polymers with
a) an organofuncational silane compound, and also a free-radical generator, and shaping the material, in a subsequent step, with addition of at least one silicon-containing precursor compound of an organic acid, one organic acid, and/or one silicon-free precursor compound containing an organic acid, and then crosslinking the material with exposure to moisture.

11. A process for producing compounded polymer materials, by
1) reacting a mixture made of thermoplastic parent polymer with component B of the masterkit and component A of the masterkit of Embodiment 9, in a compounding apparatus, or
2) reacting a mixture made of thermoplastic parent polymer in a first step with component B of the masterkit of Embodiment 9, and shaping the material in a subsequent step, with addition of component A of the masterkit of Embodiment claim 9, and crosslinking the material with exposure to moisture, or
3) reacting a mixture made of monomer and/or prepolymer of the thermoplastic parent polymers with component B of the masterkit of Embodiment 9, and shaping the material in a subsequent step, with addition of component A of the masterkit of Embodiment 9, and then crosslinking the material with exposure to moisture, or
4) reacting a mixture made of thermoplastic parent polymer with the composition of Embodiments 1 to 9, or a masterkit of Embodiment 9, in a monosil process, or
5) reacting a mixture made of thermoplastic parent polymer with the composition of Embodiments 1 to 8, or a masterkit of Embodiment 9, in a sioplas process, or
6) reacting a mixture made of monomer and/or prepolymer of the thermoplastic parent polymers with the composition as claimed in any of claims 1 to 8, or a masterkit of Embodiment 9, in a copolymerization process.

12. The process of Embodiment 10 or 11,
characterized in
that the composition of any of Embodiment 1 to 8, or a masterkit of Embodiment 9 is used in the production of silane-grafted or silane-copolymerized, and/or filled or unfilled compounded polymer materials, and/or crosslinked, filled, or crosslinked, unfilled polymers.

13. A polymer, a compounded polymer material, or an unfilled or filled plastic, obtainable by any of Embodiment 10 to 12.

14. A molding obtainable by any of Embodiment 1 to 13.

15. A polymer kit comprising the composition of any of Embodiment 1 to 8, and/or a masterkit of Embodiment 9, and also, in particular separately therefrom, as further components, a thermoplastic parent polymer, a silane-grafted parent polymer, a silane-copolymerized parent polymer, a monomer, or prepolymer of the parent polymer, and/or a mixture of these.

16. The use of the composition of any of Embodiment 1 to 8, of the masterkit of Embodiment 9, or of the polymer kit of Embodiment 15, for producing filled and/or unfilled compounded polymer materials, and/or crosslinked, filled, or crosslinked, unfilled polymers based on thermoplastic parent polymers.

DETAILED DESCRIPTION OF THE INVENTION

Surprisingly, it has been found that the composition which comprises at least one hydrolyzable precursor compound of an organic acid, and also, if appropriate, an organofunctional silane compound, can be reacted in a simple and cost-effective manner with thermoplastic parent polymers, monomers, and/or prepolymers of the parent polymers, to give compounded polymer materials, and does not have the abovementioned disadvantages, such as toxicity and odor impairment. Another factor, dependent on the composition, is that there is then overall no liberation of alcohols in the process for producing compounded polymer materials. —By way of example, when at least one silicon-containing precursor compound of an organic acid, for example of the general formula I, where $z=1$, 2, or 3, and/or II, where $y=0$, 1, 2, or 3, and/or where $z=0$, and $OR^1$ corresponds to an unsaturated carboxylate moiety, is grafted onto a parent polymer, or is copolymerized with a monomer and/or prepolymer of the parent polymer, if appropriate in the presence of a free-radical generator, or is mixed with a corresponding carboxy-substituted silane-grafted parent polymer and, if appropriate, after the shaping process a crosslinking process takes place in the presence of moisture. The grafting process or copolymerization process can also take place in the presence of an organofunctional silane compound, an example being an unsaturated alkoxysilane of the general formula III.

The invention therefore provides a composition which comprises, as components of group a), at least one silicon-containing precursor compound of an organic acid, and/or one organofunctional silane compound and, if appropriate, as components of group b), one organic acid, and one silicon-free precursor compound containing an organic acid, an example being an alkali-metal or, respectively, alkaline-earth-metal salt of an organic acid, sodium myristate, magnesium dimyristate, sodium laurate, magnesium laurate, sodium stearate, magnesium distearate; or an anhydride or ester, examples being the triglycerides that occur in fats and in oils.

Particularly preferred compositions comprise, as components, at least one organofunctional silane compound and, selected from the group of the acids or precursor compounds of the acids, at least one silicon-containing precursor compound of an organic acid, and/or one organic acid, and/or one silicon-free precursor compound containing organic acid. By way of example, said preferred composition can comprise an unsaturated alkoxysilane of the general formula III, an example being vinylalkoxysilane, and a compound of the general formula I and/or II, and/or one of the fatty acids mentioned hereinafter.

Alternative preferred compositions comprise, from the group of the acids or precursor compounds of the acids, at least one silicon-containing precursor compound of an organic acid, and/or one organic acid, and/or one silicon-free precursor compound at least two of the compounds mentioned, i.e. of the precursor compounds or acid and, if appropriate, at least one organofunctional silane compound.

One example of these types of compositions is a silicon-containing precursor compound of an organic acid, an example being a carboxy-substituted silane, e.g. vinyltristearylsilane and, as second compound, an organic acid, such as myristic acid or oleic acid. Another example is a composition comprising a tetracarboxy-substituted silane, such as tetramyristylsilane, tetralaurylsilane, tetracaprinylsilane, or corresponding mixed silanes, or a mixture of the silanes with myristic acid, capric acid, lauric acid, and/or else behenic acid.

Compositions of the invention are suitable for use in a monosil process or sioplas process with thermoplastic parent polymers, or in a copolymerization process with monomers and/or prepolymers of thermoplastic parent polymers.

Thermoplastic parent polymers for the purposes of the invention are in particular acrylonitrile-butadiene-styrene (ABS), polyamides (PA), polymethyl methacrylate (PMMA), polycarbonate (PC), polyethylene (PE), polypropylene (PP), polystyrene (PS), polyvinyl chloride (PVC), and also ethylene-vinyl acetate copolymers (EVA), EPDM, or EPM, which are polymers based on ethylene units, and/or celluloid, or silane-copolymerized polymers, and monomers and/or prepolymers are precursor compounds of said parent polymers, examples being ethylene and propylene. Other thermoplastic parent polymers are mentioned below.

In particular, the composition is in essence anhydrous, in order to suppress any undesired hydrolysis and/or condensation prior to the actual use in the monosil process or sioplas process, or cocondensation process.

The composition comprises, as component of group a), at least one
i) silicon-containing precursor compound of an organic acid of the general formula I and/or II, and/or
ii) an organofunctional silane compound which corresponds to an unsaturated alkoxysilane,
where i) corresponds to the general formula I and/or II

$(A)_z SiR^2_x (OR^1)_{4-z-x}$ (I)

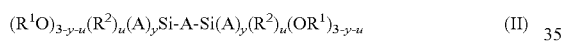

$(R^1O)_{3-y-u}(R^2)_u(A)_y Si\text{-}A\text{-}Si(A)_y(R^2)_u(OR^1)_{3-y-u}$ (II)

where, mutually independently, z is 0, 1, 2, or 3, x is 0, 1, 2, or 3, y is 0, 1, 2, or 3, and u is 0, 1, 2, or 3, with the proviso that in formula I z+x is smaller than or equal to 3, and in formula II y+u is independently smaller than or equal to 2, and preference is given to the tricarboxysilanes of the formula I where z=1, x=0 or, z=0 and x=1, and/or tetracarboxysilanes where z=0 and x=0, are suitable, as also are the dicarboxysilanes, where z=1 and x=1,
where A is mutually independently in formula I and/or II a monovalent olefin group, particular examples being $(R^9)_2C\!=\!C(R^9)\text{-}M_k\text{-}$, in which $R^9$ are identical or different, and $R^9$ is a hydrogen atom or a methyl group or a phenyl group, the group M is a group from —CH$_2$—, —(CH$_2$)$_2$—, —(CH$_2$)$_3$—, —O(O)C(CH$_2$)$_3$—, or —C(O)O—(CH$_2$)$_3$—, k is 0 or 1, examples being vinyl, allyl, 3-methacryloxypropyl, and/or acryloxypropyl, n-3-pentenyl, n-4-butenyl, or
isoprenyl, 3-pentenyl, hexenyl, cyclohexenyl, terpenyl, squalanyl, squalenyl, polyterpenyl, betulaprenoxy, cis/trans-polyisoprenyl, or
$R^8\text{—}F_g\text{—}[C(R^8)\!=\!C(R^8)\text{—}C(R^8)\!=\!C(R^8)]_r\text{—}F_g\text{—}$, in which $R^8$ are identical or different, and $R^8$ is a hydrogen atom or an alkyl group having from 1 to 3 carbon atoms, or an aryl group, or an aralkyl group, preferably a methyl group or a phenyl group, groups F are identical or different, and F is a group from —CH$_2$—, —(CH$_2$)$_2$—, —(CH$_2$)$_3$—, —O(O)C(CH$_2$)$_3$—, or —C(O)O—(CH$_2$)$_3$—, r is from 1 to 100, in particular 1 or 2, and g is 0 or 1,
and where A takes the form of a divalent olefin moiety in formula II, examples being the corresponding alkenylenes, such as 2-pentenylene, 1,3-butadienylene, iso-3-butenylene, pentenylene, hexenylene, hexenedienylene, cyclohexenylene, terpenylene, squalanylene, squalenylene, polyterpenylene, cis/trans-polyisoprenylene, $R^1$ in formula I and/or II corresponds mutually independently to a carbonyl-$R^3$ group, i.e. a —(CO)$R^3$ group (—(C=O)—$R^3$), so that —OR$^1$ is —O(CO)$R^3$, where $R^3$ corresponds to a hydrocarbon moiety having from 1 to 45 carbon atoms, in particular to an unsubstituted or substituted hydrocarbon moiety (HC moiety) having from 4 to 45 carbon atoms, in particular having from 6 to 45 carbon atoms, preferably having from 6 to 22 carbon atoms, particularly preferably having from 6 to 14 carbon atoms, with preference having from 8 to carbon atoms, and in particular to a linear, branched, and/or cyclic unsubstituted and/or substituted hydrocarbon moiety, and particularly preferably to a hydrocarbon moiety of a natural or synthetic fatty acid, and in particular $R^3$ in $R^1$ is, mutually independently, a saturated HC moiety using —$C_nH_{2n+1}$, where n=4 to 45, examples being —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_{19}H_{39}$, —$C_{20}H_{41}$, —$C_{21}H_{43}$, —$C_{22}H_{45}$, —$C_{23}H_{47}$, —$C_{24}H_{49}$, —$C_{25}H_{51}$, —$C_{26}H_{53}$, —$C_{27}H_{55}$, —$C_{28}H_{57}$, —$C_{29}H_{59}$, or else preferably an unsaturated HC moiety, examples being —$C_{10}H_{19}$, —$C_{15}H_{29}$, —$C_{17}H_{33}$, —$C_{17}H_{33}$, —$C_{19}H_{37}$, —$C_{21}H_{41}$, —$C_{21}H_{41}$, —$C_{21}H_{41}$, —$C_{23}H_{45}$, —$C_{17}H_{31}$, —$C_{17}H_{29}$, —$C_{17}H_{29}$, —$C_{19}H_{31}$, —$C_{19}H_{29}$, —$C_{21}H_{33}$ and/or —$C_{21}H_{31}$. The composition can likewise use the relatively short-chain HC moieties $R^3$, examples being —$C_4H_9$, —$C_3H_7$, —$C_2H_5$, —$CH_3$ (acetyl) and/or $R^3$=H (formyl). However, because of the low hydrophobicity of the HC moieties, the composition is generally based on compounds of the formula I and/or II in which $R^1$ is a carbonyl-$R^3$ group selected from the group of $R^3$ having an unsubstituted or substituted hydrocarbon moiety having from 4 to 45 carbon atoms, in particular having from 6 to 22 carbon atoms, preferably having from 8 to 22 carbon atoms, particularly preferably having from 6 to 14 carbon atoms, or with preference having from 8 to 13 carbon atoms.

$R^2$ is mutually independently a hydrocarbon group, in particular a substituted or unsubstituted linear, branched, and/or cyclic alkyl, alkenyl, alkylaryl, alkenylaryl, and/or aryl group having from 1 to 24 carbon atoms, preferably having from 1 to 18 carbon atoms, and in particular having from 1 to 3 carbon atoms in the case of alkyl groups. Particularly suitable alkyl groups are ethyl groups, n-propyl groups, and/or isopropyl groups. Suitable substituted hydrocarbons are in particular halogenated hydrocarbons, examples being 3-halopropyl, such as 3-chloropropyl or 3-bromopropyl groups, where these are, if appropriate, accessible to nucleophilic substitution or else improve processability.

It is therefore preferably also possible to use silicon-containing precursor compounds of an organic acid of the general formula I and/or II which correspond to alkyl-substituted di- or tricarboxysilanes where z=0 and x=1 or 2. Examples here are methyl-, dimethyl-, ethyl-, or methylethyl-substituted carboxysilanes based on capric acid, myristic acid, oleic acid, or lauric acid.

Carbonyl-$R^3$ groups are the acid moieties of the organic carboxylic acids, an example being $R^3$—(CO)—, where these in the form of carboxy groups in accordance with the formulae have bonding to the silicon Si—OR$^1$, as set out above. The acid moieties of the formula I and/or II can generally be obtained from naturally occurring or synthetic fatty acids, examples being the saturated fatty acids valeric acid (pentanoic acid, R$^3$=C$_4$H$_9$), caproic acid (hexanoic acid, R$^3$=C$_5$H$_{11}$), enanthic acid (heptanoic acid, R$^3$=C$_6$$^{14}$$_{13}$), caprylic acid (octanoic acid, R$^3$=C$_7$H$_{15}$), pelargonic acid (nonanoic acid, R$^3$=C$_8$H$_{17}$) capric acid (decanoic acid, R$^3$=C$_9$H$_{19}$), lauric acid (dodecanoic acid, R$^3$=C$_9$H$_{19}$), undecanoic acid (R$^3$=C$_{10}$H$_{23}$), tridecanoic acid (R$^3$=C$_{12}$H$_{25}$), myristic acid (tetradecanoic acid, R$^3$=C$_{13}$H$_{27}$), pentadecanoic acid (R$^3$=C$_{14}$H$_{29}$), palmitic acid (hexadecanoic acid, R$^3$=C$_{15}$H$_{31}$), margaric acid (heptadecanoic acid, R$^3$=C$_{16}$H$_{33}$)/stearic acid (octadecanoic acid, R$^3$=C$_{17}$H$_{35}$), nonadecanoic acid (R$^3$=C$_{18}$H$_{37}$), arachic acid (eicosanoic/icosanoic acid, R$^3$=C$_{19}$H$_{39}$), behenic acid (docosanoic acid, R$^3$=C$_{21}$H$_{43}$), lignoceric acid (tetracosanoic acid, R$^3$=C$_{23}$H$_{47}$), cerotinic acid (hexacosanoic acid, R$^3$=C$_{25}$H$_{51}$), montanic acid (octacosanoic acid, R$^3$=C$_{27}$H$_{55}$), and/or melissic acid (triacontanoic acid, R$^3$=C$_{29}$H$_{59}$), and also the short-chain unsaturated fatty acids, such as valeric acid (pentanoic acid, R$^3$=C$_4$H$_9$), butyric acid (butanoic acid, R$^3$=C$_3$H$_7$), propionic acid (propanoic acid, R$^3$=C$_2$H$_5$), acetic acid (R$^3$=CH$_3$), and/or formic acid (R$^3$=H), and can be used as silicon-containing precursor compound of the formula I and/or II of the otherwise purely organic silanol condensation catalysts.

It is however preferable, in the formula I and/or II, to use fatty acids having a hydrophobic HC moiety, where these are sufficiently hydrophobic, do not exhibit any unpleasant odor after liberation, and do not exude from the polymers produced. By way of example, said exudation restricts the possible use of relatively high concentrations of stearic acid and palmitic acid. By way of example, at a concentration above a value as low as about 0.01% by weight of the liberated stearic acid or palmitic acid, based on the overall constitution of the polymer, a waxy exudation is observed on the polymers produced. Preferred acids in the formulae I and/or II are therefore capric acid, lauric acid, and myristic acid, but behenic acid can also be used with advantage.

The naturally occurring or synthetic unsaturated fatty acids can similarly preferably be converted to the precursor compounds of the formula I and/or II. They can simultaneously perform two functions, firstly serving as silanol condensation catalyst, and, by virtue of their unsaturated hydrocarbon moieties, participating directly in the free-radical polymerization reaction. Preferred unsaturated fatty acids are sorbic acid (R$^3$=C$_5$H$_7$), undecylenic acid (R$^3$=C$_{10}$H$_{19}$), palmitoleic acid (R$^3$=C$_{15}$H$_{29}$), oleic acid (R$^3$=C$_{17}$H$_{33}$), elaidic acid (R$^3$=C$_{17}$H$_{33}$), vaccenic acid (R$^3$=C$_{19}$H$_{37}$), icosenoic acid (R$^3$=C$_{20}$H$_{39}$), cetoleic acid (R$^3$=C$_{21}$H$_{41}$), erucic acid (R$^3$=C$_{21}$H$_{41}$), nervonic acid (R$^3$=C$_{23}$H$_{45}$), linoleic acid (R$^3$=C$_{17}$H$_{31}$) alpha-linolenic acid (R$^3$=C$_{17}$H$_{29}$), gamma-linolenic acid (R$^3$=C$_{17}$H$_{29}$) arachidonic acid (R$^3$=C$_{19}$H$_{31}$) timnodonic acid (R$^3$=C$_{19}$H$_{29}$) clupanodonic acid (R$^3$=C$_{21}$H$_{33}$), ricinoleic acid (12-hydroxy-9-octadecenoic acid (R$^3$=C$_{17}$H$_{33}$) and/or cervonic acid (R$^3$=C$_{21}$H$_{31}$).

Other advantageous acids from which the precursor compounds of the formula I and/or II having R$^3$—COO or R$^1$O can be produced are glutaric acid, lactic acid (R$^1$ being (CH$_3$)(HO)CH—), citric acid (R$^1$ being HOOCCH$_2$(COOH)(OH)CH$_2$—), vulpinic acid, terephthalic acid, gluconic acid, and adipic acid, where it is also possible that all of the carboxy groups have been Si-functionalized, benzoic acid (R$^1$ being phenyl), nicotinic acid (vitamin B3, B5). However, it is also possible to use the natural or synthetic amino acids, in such a way that R$^1$ corresponds to appropriate moieties such as those deriving from tryptophan, L-arginine, L-histidine, L-phenylalanine, or L-leucine, where L-leucine can be used with preference. It is also correspondingly possible to use the corresponding D-amino acids or a mixture of L- and D-amino acids, or an acid such as D[(CH$_2$)$_d$)COOH]$_3$, where D=N, P, and d is from 1 to 12, preferably 1, 2, 3, 4, 5, or 6, where the hydroxy group of each carboxylic acid function can independently have been Si-functionalized.

The composition can therefore also comprise corresponding compounds of the formula I and/or II based on moieties of said acids.

The silicon-containing precursor compound of an organic acid is in particular active in hydrolyzed form as silane hydrolysis catalyst and/or silane condensation catalyst, and is also itself suitable in hydrolyzed or nonhydrolyzed form for grafting on a polymer and/or copolymerization with a parent polymer, polymer/monomer, or prepolymer. In hydrolyzed form, the silanol compound formed contributes to crosslinking by means of resultant Si—O—Si siloxane bridges during the condensation reaction. Said crosslinking can use other silanols, siloxanes, or can generally use functional groups which are present on substrates, on fillers, and/or on carrier materials and which are suitable for the crosslinking reaction. Preferred fillers and/or carrier materials are therefore aluminum hydroxides, magnesium hydroxides, fumed silica, precipitated silica, silicates, and also other fillers and carrier materials mentioned below.

Very particularly preferably the inventive composition comprises, as component (i) in group a), vinylsilane trimyristate, vinylsilane trilaurate, vinylsilane tricaprate, or else corresponding allylsilane compounds of the abovementioned acids, and/or silane tetracarboxylates Si(OR$^1$)$_4$, examples being silane tetramyristate, silane tetralaurate, and silane tetra-caprate, and it can also be advantageous to add a certain amount of vinylsilane tristearate, vinylsilane tripalmitate, allylsilane tristearate, and/or allylsilane tripalmitate. The amounts used of silane stearates and/or silane palmitates should preferably be such that no more than 1.0% by weight, preferably from 0.001% by weight to 0.8% by weight, in particular from 0.01% to 0.6% by weight, of liberated acid, such as stearic acid or palmitic acid, is present in the overall constitution in % by weight of the resultant compounded polymer material or polymer. A corresponding limit also applies when adding free stearic and/or palmitic acid.

Particular preference is always given to those compounds of group a) and/or b) in which the organic acid has at least one hydrophobic group which permits solvation or dispersibility in respect of the plastic. These are in particular long-chain, branched or cyclic, nonpolar, in particular unsubstituted hydrocarbon moieties, in particular having from 6 to 22 carbon atoms, preferably having from 8 to 14 carbon atoms, particularly preferably having from 8 to 13 carbon atoms, having at least one carboxylic acid group. Preferred substituted hydrocarbon moieties that can be used are halogen-substituted HC moieties.

As indicated above, the composition comprises, as component of group a), at least one i) silicon-containing precursor compound of an organic acid of the general formula I and/or II, and/or ii) one organofunctional silane compound which corresponds to an unsaturated or olefinic alkoxysilane, where the silane compound II) particularly preferably corresponds to a monounsaturated alkoxysilane.

For the purposes of the present invention, the organofunctional silane compound is particularly suitable for grafting on a polymer and/or for copolymerization with a monomer, prepolymer, or parent polymer, and subsequent moisture-crosslinking. For the purposes of the present invention, it is preferable that the silicon-containing precursor compound I and/or II is also suitable for grafting on a polymer and/or copolymerization with a monomer, prepolymer, or parent polymer, and subsequent moisture-crosslinking.

The production of the carboxysilanes has long been known to the person skilled in the art. By way of example, U.S. Pat. No. 4,028,391 discloses processes for their production in which chlorosilanes are reacted with fatty acids in pentane. U.S. Pat. No. 2,537,073 discloses another process. The acid can, for example, be heated directly in a nonpolar solvent, such as pentane, with trichlorosilane or with a functionalized trichlorosilane, at reflux, to give the carboxysilane. In an example for production of tetracarboxysilanes, tetrachlorosilane is reacted with the corresponding acid in a suitable solvent (Zeitschrift für Chemie (1963), 3(12), 475-6). Other processes relate to the reaction of the salts or anhydrates of the acids with tetrachlorosilane or with functionalized trichloro-silanes.

As organofunctional silane compound II) of group a) it is in particular possible to use a compound corresponding to the general formula III,

where, mutually independently, b is 0, 1, 2, or 3, and a is 0, 1, 2, or 3, with the proviso that in formula III a+b is smaller than or equal to 3, where B, mutually independently, is a monovalent $(R^7)_2C=C(R^7)-E_q-$ group in formula III, in which $R^7$ are identical or different, and $R^7$ is a hydrogen atom or a methyl group or a phenyl group, the group E is a group from —CH$_2$—, —(CH$_2$)$_2$—, —(CH$_2$)$_3$—, —O(O)C(CH$_2$)$_3$—, or —C(O)O—(CH$_2$)$_3$—, q is 0 or 1, examples being vinyl, allyl, n-3-pentyl, n-4-butenyl, 3-methacryloxy-propyl, and/or acryloxypropyl, or isoprenyl, hexenyl, cyclohexenyl, terpenyl, squalanyl, squalenyl, polyterpenyl, betulaprenoxy, cis/trans-polyisoprenyl, or B comprises an olefin group, for example $R^6-D_p-[C(R^6)=C(R^6)-C(R^6)=C(R^6)]_t-D_p-$, in which $R^6$ are identical or different, and $R^6$ is a hydrogen atom or an alkyl group having from 1 to 3 carbon atoms, or an aryl group, or an aralkyl group, preferably a methyl group or a phenyl group, the groups D are identical or different, and D is a group from —CH$_2$—, —(CH$_2$)$_2$—, —(CH$_2$)$_3$—, —O(O)C(CH$_2$)$_3$—, or —C(O)O—(CH$_2$)$_3$—, and p is 0 or 1, and t is 1 or 2.

$R^5$ is, mutually independently, methyl, ethyl, n-propyl, or isopropyl, $R^4$ is, mutually independently, a substituted or unsubstituted hydrocarbon group, in particular a substituted or unsubstituted linear, branched, and/or cyclic alkyl, alkenyl, alkylaryl, alkenyl-aryl, and/or aryl group having from 1 to 24 carbon atoms, in particular having from 1 to 16 carbon atoms, preferably having from 1 to 8 carbon atoms. In particular, the substituted groups are hydrophobic.

A particularly suitable alkyl group is an ethyl, n-propyl, isopropyl, n-butyl, isobutyl, cyclohexyl, n-octyl, isooctyl, or hexadecyl group, and a particularly suitable substituted alkyl group is a haloalkyl group having chlorine substituents or bromine substituents, preference being given to haloalkyl groups suitable for nucleophilic substitution, examples being 3-chloropropyl groups or 3-bromopropyl groups.

In particular if the composition has no components of group b), it is particularly preferable that B comprises at least one olefin group, an example being polyethylene, polypropylene, propylene copolymer, or ethylene copolymer, if appropriate together with a free-radical generator and with other stabilizers and/or additives.

It is very particularly preferable that the inventive composition comprises, as component (ii), vinyltrimethoxysilane, vinyltriethoxysilane, vinylmethyldialkoxysilane, vinyltriethoxymethoxysilane (VTMOEO), vinyltriisopropoxysilane, vinyltri-n-butoxysilane, 3-methacryloxypropyltriethoxysilane, 3-methacryloxypropyltrimethoxysilane (MEMO), and/or vinylethoxydimethoxysilane, and/or allylalkoxysilanes, such as allyltriethoxysilane, or unsaturated siloxanes, preferred examples being oligomeric vinylsiloxanes, or a mixture of the abovementioned compounds. Preferred organofunctional silane compounds contain either a vinyl group or methacrylic group, since these compounds are reactive toward free radicals and are suitable for grafting onto a polymer chain or for copolymerization with monomers or with prepolymers.

The form taken by the composition is usually liquid. However, it is preferable, for greater ease of metering, that the composition is provided in the form of solid, flowable formulation, for example on a carrier material and/or filler. The carrier can be porous, particulate, swellable or, if appropriate, take the form of a foam. Suitable carrier materials are in particular polyolefins, such as PE, PP, EVA, or polymer blends, and suitable fillers are in particular inorganic or mineral fillers which can advantageously have reinforcing, extending, or else flame-retardant effect. The carrier materials and fillers are specified in more detail below.

In one preferred embodiment, the composition is composed of a selection i) of a precursor compound of the formula I and/or II, and/or ii) of a monounsaturated alkoxysilane, and/or of an organic acid, and/or of a free-radical generator and also, if appropriate, of at least one stabilizer and/or additional substance, and/or a mixture of these.

In another preferred embodiment, the composition is composed of a selection i) of a precursor compound of the formula I and/or II, where $R^1$ corresponds to a carbonyl-$R^3$ group where $R^3$ is from 4 to 45 carbon atoms, preferably having from 6 to 45 carbon atoms, in particular having from 6 to 22 carbon atoms, preferably having from 8 to 22 carbon atoms, particularly preferably having from 6 to 14 carbon atoms, with particular preference where $R^3$ is from 8 to 13 carbon atoms, in particular where $R^3$ is from 11 to 13 carbon atoms, and/or ii) of an olefinic alkoxysilane, and/or of a free-radical generator, and also, if appropriate, of at least one stabilizer and/or additional substance, and/or a mixture of these.

In alternative preferred embodiments, the composition is composed of a selection i) of a precursor compound of the formula I and/or II, in particular where $R^1$ corresponds to a carbonyl-$R^3$ group where $R^3$ is from 4 to 45 carbon atoms, preferably having from 6 to 45 carbon atoms, in particular having from 6 to 22 carbon atoms, preferably having from 8 to 22 carbon atoms, particularly preferably having from 6 to 14 carbon atoms, with particular preference where $R^3$ is from 11 to carbon atoms, and/or ii) of an olefinic alkoxysilane, and also, if appropriate, of at least one stabilizer and/or additional substance, and/or a mixture of these.

As at least one organic acid can comprise as components in group b):

iii.a) a saturated and/or unsaturated fatty acid (naturally occurring or synthetic)

an example being valeric acid, caproic acid, enanthic acid, caprylic acid, pelargonic acid, capric acid, lauric acid, undecanoic acid, tridecanoic acid, myristic acid, pentadecanoic acid, palmitic acid, margaric acid, stearic acid, nonadecanoic acid, arachic acid, behenic acid, lignoceric acid, cerotinic acid, montanic acid, melissic acid, valeric acid, butyric acid, propionic acid, acetic acid, formic acid, undecylenic acid, palmitoleic acid, oleic acid, elaidic acid, vaccenic acid, icosenoic acid, cetoleic acid, erucic acid, nervonic acid, linoleic acid, alpha-linolenic acid, gamma-linolenic acid, arachidonic acid, timnodonic acid, clupanodonic acid, cervonic acid, lignoceric acid ($H_3C$—$(CH_2)_{22}$—COOH), cerotinic acid, lactic acid, citric acid, benzoic acid, nicotinic acid, arachidonic acid (5,8,11,14-eicosatetraenoic acid, $C_{20}H_{32}O_2$), erucic acid (cis-13-docosenoic acid, $H_3C$—$(CH_2)_7$—CH=CH—$(CH_2)_{11}$—COOH), gluconic acid, icosenoic acid ($H_3C$— $(CH_2)_7$—CH=CH— $(CH_2)_9$—COOH), ricinoleic acid (12-hydroxy-9-octadecenoic acid), sorbic acid ($C_6H_8O_2$), and/or naturally occurring or else synthetic amino acids, such as tryptophan, L-arginine, L-histidine, L-phenylalanine, or L-leucine, where L-leucine is preferred, a dicarboxylic acid, such as adipic acid, glutaric acid, terephthalic acid (benzene-1,4-dicarboxylic acid), where lauric acid and myristic acid are preferred, or an acid such as $D[(CH_2)_d)COOH]_3$, where D=N, P, and n=1 to 12, preferably 1, 2, 3, 4, 5, or 6, and/or as iii.b) an acid-containing silicon-free precursor compound, an example being an organic anhydride or an ester, in particular of the abovementioned acids, or else natural or synthetic triglycerides and/or phosphoglycerides.

In general terms, the acids having relatively long hydrophobic hydrocarbon moieties, beginning with valeric acid, and preferably capric acid, lauric acid, and/or myristic acid, have good suitability as silanol condensation catalyst. The less hydrophobic acids are regarded merely as useful for the reaction with thermoplastic hydrophobic polymers, examples being propionic acid, acetic acid, and formic acid. Correspondingly, the fatty acids that have strong odors, for example butyric acid and caprylic acid are also only useful or have low to zero suitability for use in a composition, masterkit, polymer kit, or a process of the invention, because of the pungent odor. This is particularly applicable when the resultant polymers or compounded polymer materials are intended for further use in the production of drinking-water pipes.

Organic acids are carboxylic acids which have no sulfate groups or sulfonic acid groups, and in particular they are organic acids corresponding to $R^3$—COOH; the anhydrides, esters, or salts of these organic acids can also be regarded as silicon-free precursor compound, and they particularly preferably have a long-chain, nonpolar, in particular substituted or unsubstituted hydrocarbon moiety, where the hydrocarbon moiety can be saturated or unsaturated, for example where $R^3$ is from 1 to 45 carbon atoms, in particular having from 4 to 45 carbon atoms, preferably having from 8 to 45 carbon atoms, in particular having from 6 to 22 carbon atoms, preferably having from 8 to 22 carbon atoms, particularly preferably having from 6 to 14 carbon atoms, with particular preference where $R^3$ is from 8 to 13 carbon atoms, where particular preference is given to $R^3$ being from 11 to 13 carbon atoms; an example of these materials is lauric acid or myristic acid; or hydrogen ($R^3$) and at least one carboxylic acid group (COOH). Materials explicitly excluded from the definition of the organic acids are organic arylsulfonic acids, such as sulfophthalic acid, and also naphthalenedisulfonic acids.

Marked preference is therefore given to those acids having long-chain, hydrophobic hydrocarbon moieties. These acids can also function as dispersing agents and/or processing aids. In general terms, the acids that can be used in the form of organic acids as silanol condensation catalyst comprise the naturally occurring or synthetic fatty acids, examples being the following saturated fatty acids: valeric acid (pentanoic acid, $R^3$=$C_4H_9$), caproic acid (hexanoic acid, $R^3$=$C_5H_{11}$), enanthic acid (heptanoic acid, $R^3$=$C_6H_{13}$), caprylic acid (octanoic acid, $R^3$=$C_7H_{15}$), pelargonic acid (nonanoic acid, $R^3$=$C_8H_{17}$), capric acid (decanoic acid, $R^3$=$C_9H_{19}$), undecanoic acid ($R^3$=$C_{10}H_{23}$) tridecanoic acid ($R^3$=$C_{12}H_{25}$), lauric acid (dodecanoic acid, $R^3$=$C_9H_{19}$), myristic acid (tetradecanoic acid, $R^3$=$C_{13}H_{27}$) pentadecanoic acid ($R^3$=$C_{14}H_{29}$) palmitic acid (hexadecanoic acid, $R^3$=$C_{15}H_{31}$) margaric acid (heptadecanoic acid, $R^3$=$C_{16}H_{33}$), stearic acid (octadecanoic acid, $R^3$=$C_{17}H_{35}$) nonadecanoic acid ($R^3$=$C_{18}H_{37}$), arachic acid (eicosanoic/icosanoic acid, $R^3$=$C_{19}H_{39}$), behenic acid (docosanoic acid, $R^3$=$C_{21}H_{43}$), lignoceric acid (tetra-cosanoic acid, $R^3$=$C_{23}^{14}{}_{47}$) cerotinic acid (hexacosanoic acid, $R^3$=$C_{25}H_{51}$) montanic acid (octacosanoic acid, $R^3$=$C_{27}H_{55}$), and/or melissic acid (triacontanoic acid, $R^3$=$C_{29}H_{59}$), and also the short-chain fatty acids, such as valeric acid (pentanoic acid, $R^3$=$C_4H_9$), butyric acid (butanoic acid, $R^3$=$C_3H_7$), propionic acid (propanoic acid, $R^3$=$C_2H_5$), acetic acid ($R^3$=$CH_3$), and/or formic acid ($R^3$=H), where the short-chain fatty acids mentioned are not suitable as dispersing agents and/or processing aids and can therefore be omitted in preferred compositions. Lauric acid and/or myristic acid are particularly preferred.

Similarly preferred is the use of naturally occurring or synthetic unsaturated fatty acids which can perform two functions, firstly serving as silanol condensation catalyst, and, by virtue of their unsaturated hydrocarbon moieties, being capable of participating directly in the free-radical polymerization reaction. Preferred unsaturated fatty acids are sorbic acid ($R^3$=$C_5H_7$), undecylenic acid ($R^3$=$C_{10}H_{19}$), palmitoleic acid ($R^3$=$C_{15}H_{29}$), oleic acid ($R^3$=$C_{17}H_{33}$), elaidic acid ($R^3$=$C_{17}H_{33}$), vaccenic acid ($R^3$=$C_{19}H_{37}$), icosenoic acid ($R^3$=$C_{20}H_{39}$; ($H_3C$—$(CH_2)_7$—CH=CH— $(CH_2)_9$—COOH)), cetoleic acid ($R^3$=$C_{21}H_{41}$), erucic acid ($R^3$=$C_{21}H_{41}$; cis-13-docosenoic acid, $H_3C$—$(CH_2)_7$—CH=CH—$(CH_2)_{11}$—COOH), nervonic acid ($R^3$=$C_{23}H_{45}$), linoleic acid ($R^3$=$C_{17}H_{31}$), alpha-linolenic acid ($R^3$=$O_{17}H_{29}$), gamma-linolenic acid ($R^3$=$C_{17}H_{29}$), arachidonic acid ($R^3$=$C_{19}H_{31}$, 5,8,11,14-eicosatetraenoic acid, $C_{20}H_{32}O_2$), timnodonic acid ($R^3$=$C_{19}H_{29}$), clupanodonic acid ($R^3$=$C_{21}H_{33}$), ricinoleic acid (12-hydroxy-9-octadecenoic acid ($R^3$=$C_{17}H_{33}O$), and/or cervonic acid ($R^3$=$C_{21}H_{31}$).

Other advantageous acids are lignoceric acid ($H_3C$—$(CH_2)_{22}$—COOH), cerotic acid, lactic acid, citric acid, benzoic acid, nicotinic acid (vitamin B3, B5), gluconic acid or a mixture of the acids. However, it is also possible to use the natural or synthetic amino acids, such as tryptophan, L-arginine, L-histidine, L-phenylalanine, or L-leucine, where L-leucine is preferred, and it is correspondingly also possible to use the corresponding D-amino acids, or a mixture of the amino acids, or a dicarboxylic acid, such as adipic acid, glutaric acid, terephthalic acid (benzene-1,4-dicarboxylic acid), or else an acid such as $D[(CH_2)_n COOH]_3$, where D=N, and P and n=from 1 to 12, preferably 1, 2, 3, 4, 5, or 6. The corresponding anhydrides, esters or salts, for example alkali-metal salts, alkaline-earth-metal salts, or ammonium salts, of these acids can likewise be used.

In general terms it is also possible that the acid-containing silicon-free precursor compound used comprises esters and/or lactones, in particular of the abovementioned acids or, for example, the triglycerides that occur in fats or in oils, particular examples being neutral fats, or else phosphoglycerides, such as lecithin, phosphatidylethanolamine, phosphatidyl-inositol, phosphatidylserine, and/or diphosphatidyl-glycerol. It is also possible to use synthetic triglycerides, alongside naturally occurring triglycerides of vegetable origin and of animal origin.

A general requirement placed upon the precursor compound (silicon-containing and/or silicon-free) is that it is hydrolyzable under the conditions of the monosil and/or sioplas process, and thus liberates the free organic acid. It is preferable that the onset of the hydrolysis does not precede the crosslinking step of the processes, and that in particular it occurs after the shaping process, for example with introduction into the waterbath, or after the shaping process in the presence of moisture. Compounds excluded from the silicon-free precursor compounds are advantageously those which when hydrolyzed give an inorganic and an organic acid. An inorganic acid here does not include a silanol. By way of example, the term silicon-free precursor compounds does not cover acyl chlorides or in general terms corresponding acyl halides of the abovementioned organic acids. Nor are organic acid peroxides to be understood as silicon-free precursor compound.

One preferred composition which is particularly suitable for producing compounded polymer materials comprises, as component c), at least one free-radical generator. Preferred free-radical generators are organic peroxides and/or organic peresters, or a mixture of these, preferred examples being tert-butyl peroxypivalate, tert-butyl 2-ethylperoxyhexanoate, dicumyl peroxide, di-tert-butyl peroxide, tert-butyl cumyl peroxide, 1,3-di(2-tert-butylperoxyisopropyl)benzene, 2,5-dimethyl-2,5-bis(tert-butylperoxy)hex-3-yne, di-tert-amyl peroxide, 1,3,5-tris(2-tert-butylperoxy-isopropyl) benzene, 1-phenyl-1-tert-butylperoxyphthalide, alpha, alpha'-bis(tert-butylperoxy)diisopropyl-benzene, 2,5-dimethyl-2,5-di-tert-butylperoxyhexane, 1,1-di(tert-butylperoxy)-3,3,5-trimethylcyclohexane (TMCH). It can also be advantageous to use n-butyl 4,4-di(tert-butylperoxy) valerate, ethyl 3,3-di(tert-butylperoxy)butyrate, and/or 3,3, 6,9,9-hexamethyl-1,2,4,5-tetraoxacyclononane.

The composition can moreover comprise, as component d), at least one stabilizer and/or other additional substance, and/or a mixture of these. The stabilizer and/or other additional substances used can, if appropriate, comprise metal deactivators, processing aids, inorganic or organic pigments, fillers, carrier materials, and adhesion promoters. Examples of these are titanium dioxide ($TiO_2$), talc, clay, quartz, kaolin, aluminum hydroxide, magnesium hydroxide, bentonite, montmorillonite, mica (muscovite mica), calcium carbonate (chalk, dolomite), dyes, pigments, talc, carbon black, $SiO_2$, precipitated silica, fumed silica, aluminum oxides, such as alpha- and/or gamma-aluminum oxide, aluminum oxide hydroxides, boehmite, baryte, barium sulfate, lime, silicates, aluminates, aluminum silicates, and/or ZnO, or a mixture of these. It is preferable that the carrier materials or additional substances, such as pigments or fillers, are pulverulent, particulate, porous, or swellable or, if appropriate, take the form of a foam.

Examples of preferred metal deactivators are N,N'-bis(3-(3,5-di-tert-butyl-4-hydroxyphenyl)propion-yl)hydrazine, and also tris(2-tert-butyl-4-thio(2'-methyl-4-hydroxy-5'-tert-butyl)phenyl-5-methyl)phenyl phosphite.

The composition can moreover comprise, as additional component, at least one heat stabilizer, an example being pentaerythritol tetrakis[3-(3,5-bis(1,1-dimethylethyl)-4-hydroxyphenyl)propionate], octadecyl 3-(3,5-di-tert-butyl-4-hydroxyphenyl)propionate, or else 4,4'-bis(1,1-dimethylbenzyl)diphenylamine.

The fillers are generally inorganic or mineral fillers and can advantageously have reinforcing, extending, or else flame-retardant effect. At least at their surfaces, they bear groups which can react with the alkoxy groups of the unsaturated organosilane/mixtures. The result of this can be that the silicon atom, with the functional group bonded thereto, becomes chemically fixed on the surface. Particular examples of groups of this type on the surface of the filler are hydroxy groups.

Preferred fillers are accordingly metal hydroxides having a stoichiometric proportion of hydroxy groups or, in the various dehydrated forms thereof, having a substoichiometric proportion of hydroxy groups, extending as far as oxides having comparatively few residual hydroxy groups, where these are however detectable by DRIFT-IR spectroscopy.

Examples of suitable fillers are aluminum trihydroxide (ATH), aluminum oxide hydroxide (AlOOH.aq), magnesium dihydroxide (MDH), brucite, huntite, hydromagnesite, mica, and montmorillonite. Other fillers that can be used are calcium carbonate, talc, and also glass fibers. It is also possible to use the materials known as "char formers", examples being ammonium polyphosphate, stannates, borates, talc, or materials of these types in combination with other fillers.

The composition may comprise, as further component e), a thermoplastic parent polymer, a silane-grafted parent polymer, a silane-copolymerized parent polymer, and/or monomers and/or prepolymers of said parent polymers, or else silane block coprepolymers or block coprepolymers, and/or a mixture of these. It is preferable that the thermoplastic parent polymer is a nonpolar polyolefin, an example being polyethylene or polypropylene, or a polyvinyl chloride, or a silane-grafted polyolefin and/or silane-copolymerized polyolefin, and/or a copolymer of one or more olefins and of one or more comonomers which contain polar groups.

The thermoplastic parent polymer can also function to some extent or completely as carrier material, for example in a masterbatch, comprising, as carrier material, a thermoplastic parent polymer or a polymer and the silicon-containing precursor compound of an organic acid and an organofunctional silane compound or, in an alternative, a thermoplastic parent polymer, or a polymer and an organofunctional silane compound, in particular of the formula III, and an organic acid.

Other examples of silane-copolymerized thermoplastic parent polymers are ethylene-silane copolymers, for example ethylene-vinyltrimethoxysilane copolymer, ethylene-vinyltriethoxysilane copolymer, ethylene-dimethoxyethoxysilane copolymer, ethylene-gamma-trimethoxysilane copolymer, ethylene-gamma-(meth)acryloxypropyltriethoxysilane copolymer, ethylene-gamma-acryloxypropyltriethoxysilane copolymer, ethylene-gamma-(meth)acryloxypropyltrimethoxysilane copolymer, ethylene-gamma-acryloxypropyltrimethoxysilane copolymer, and/or ethylene-triacetoxysilane copolymer.

The nonpolar thermoplastic parent polymers used can comprise thermoplastics such as in particular an unmodified PE grade, an example being LDPE, LLDPE, HDPE, or mPE. Parent polymers bearing polar groups give by way of example improved fire performance, i.e. lower flammability and smoke density, and increase capability to accept filler. Examples of polar groups are hydroxy, nitrile, carbonyl, carboxy, acyl, acyloxy, and carbo-alkoxy groups, and amino groups, and also halogen atoms, in particular chlorine atoms. Olefinic double bonds and carbon-carbon triple bonds are nonpolar. Suitable polymers are not only polyvinyl chloride but also copolymers of one or more olefins and of one or more comonomers which contain polar groups, e.g. vinyl acetate, vinyl propionate, (meth)acrylic acid, methyl (meth) acrylate, ethyl (meth)acrylate, butyl (meth)acrylate, or acrylonitrile. Examples of the amounts of the polar groups in the copolymers are from 0.1 to 50 mol %, preferably from 5 to 30 mol %, based on the polyolefin units. Particularly suitable parent polymers are ethylene-vinyl acetate copolymers (EVA). By way of example, a suitable commercially available copolymer contains 19 mol % of vinyl acetate units and 81 mol % of ethylene units.

Particularly suitable parent polymers are polyethylene, polypropylene, and also corresponding silane-modified polymers. In particular, therefore, the use of inventive compositions or masterbatches (masterkit or polymer kit) can give silane-grafted, silane-copolymerized, and/or silane-crosslinked PE, PP, polyolefin copolymer, EVA, EPDM, or EPM in an advantageous manner. The silane-grafted polymers can be in a form filled with fillers or in an unfilled form and, if appropriate, can be moisture-crosslinked subsequently, after a shaping process. A corresponding situation applies to the silane-copolymerized polymers in a form filled with fillers or in unfilled form, and these polymers can, if appropriate, be moisture-crosslinked subsequently, after a shaping process.

The composition of the invention is suitable as additive in a monosil process, in a sioplas process, and/or in a copolymerization process. It is particularly appropriate that the silane hydrolysis catalyst and/or silanol condensation catalyst does not become active until additional moisture is added. The final crosslinking of the unfilled or filled polymer therefore generally takes place in a known manner in a waterbath, in a steam bath, or else via atmospheric moisture, at ambient temperatures (the process known as "ambient curing").

The form taken by the components of the composition, a particular example being the silicon-containing precursor compound of an organic acid, is advantageously liquid and preferably waxy or solid, or bound on a carrier material, and/or the form taken by the organofunctional silane compound can be liquid, highly viscous, waxy, or solid, or bound on a carrier material. In particular, the silicon-containing precursor compound of an organic acid is in essence waxy or solid, i.e. is in essence in solid phase, which can have amorphous or crystalline regions. This measure can make it easy to store the precursor compound in anhydrous form, and to meter the precursor compound. Undesired hydrolysis and/or condensation prior to use, in particular in a monosil process, sioplas process, or copolymerization process, can be suppressed.

In order to permit better regulation of metering capability and, if appropriate, susceptibility to hydrolysis, the silicon-containing precursor compound of an organic acid of the general formula I and/or II, the organofunctional silane compound and, if appropriate, the free-radical generator can have been applied to a carrier material, for example as described in EP 0 426 073.

To the extent that the silicon-containing precursor compound I and/or II is itself solid, it can itself be used as carrier material, in particular for an organofunctional silane, for example as a carrier material for a silane of the general formula III, for example of vinyltriethoxysilane, vinyltrimethoxysilane, vinyltris(methoxyethoxy)silane (VT-MOEO), vinyl (co)oligomers, or other liquid silanes of the formula III.

Preferable suitable carrier material is a porous polymer selected from polypropylene, polyolefins, ethylene copolymer using low-carbon alkenes, ethylene-vinyl acetate copolymer, high-density polyethylene, low-density polyethylene, or linear low-density polyethylene, where the porous polymer can have a pore volume of from 30 to 90% and in particular can be used in the form of granules or pellets.

As an alternative, the carrier material can also be a filler or additional substance, in particular a nanoscale filler. Preferred carrier materials, fillers, or additional substances are aluminum hydroxide, magnesium hydroxide, fumed silica, precipitated silica, wollastonite, calcined variants, chemically and/or physically modified materials, such as kaolin, modified kaolin, and in particular ground, exfoliating materials, such as phyllosilicates, preferably specific kaolins, a calcium silicate, a wax, such as a polyolefin wax based on LDPE (low-density polyethylene), or a carbon black.

The carrier material can encapsulate the silicon-containing precursor compound and/or the silane compound of group a), and/or the free-radical generator, or can retain these in physically or chemically bound form. It is advantageous here if the loaded or unloaded carrier material is swellable, in particular in a solvent. The amount of the silane components of group a) is usually in the range from 0.01% by weight to 99.9% by weight, preferably from 0.1% by weight to 70% by weight, preferably from 0.1% by weight to 50% by weight, with particular preference from 0.1% by weight to 30% by weight, based on the total weight of the composition comprising the carrier material, particularly preferably in the form of masterbatch. The amount present of the carrier material is therefore generally from 99.99 to 0.01% by weight, based on the total weight of the composition (giving 100% by weight).

In order to facilitate metering of the composition and protect it from premature hydrolysis, it is particularly preferable that the silicon-containing precursor compound of an organic acid, the organofunctional silane compound, or a mixture of the two compounds is in a form that is waxy or solid or bound to a carrier material.

Individual preferred carrier materials that may be mentioned are: ATH (aluminum trihydroxide, $Al(OH)_3$), magnesium hydroxide ($Mg(OH)_2$), or fumed silica, which is produced on an industrial scale via continuous hydrolysis of silicon tetrachloride in a hydrogen/oxygen flame. This process vaporizes the silicon tetrachloride which then reacts spontaneously and quantitatively within the flame with the water derived from the hydrogen/oxygen reaction. Fumed silica is an amorphous form of silicon dioxide and is a free-flowing, bluish powder. Particle size is usually in the region of a few nanometers, and specific surface area is therefore large, generally being from 50 to 600 $m^2/g$. The process by which the vinylalkoxysilanes and/or the silicon-containing precursor compound, or a mixture of these, becomes attached to the material here is therefore in essence adsorption. Precipitated silicas are generally produced from sodium waterglass solutions, via neutralization with inorganic acids under controlled conditions. After isolation from the liquid phase, washing, and drying, the crude product is finely ground, e.g. in steam-jet mills. Again, precipitated silica is a substantially amorphous silicon dioxide, the specific surface area of which is generally from 50 to 150 m$^2$/g. Unlike fumed silica, precipitated silica has a certain porosity, for example about 10% by volume. The process by which the vinylalkoxysilanes and/or the silicon-containing precursor compound, or a mixture of these, becomes attached to the material can therefore be either adsorption on the surface or absorption within the pores. Calcium silicate is generally produced industrially by fusing quartz or kieselguhr with calcium carbonate or calcium oxide, or via precipitation of aqueous sodium metasilicate solutions with water-soluble calcium compounds. The carefully dried product is generally porous and can absorb up to five times the amount by weight of water or oils.

Porous polyolefins, such as polyethylene (PE) or polypropylene (PP), and also copolymers, such as ethylene copolymers with low-carbon alkenes, such as propene, butene, hexene, or octene, or ethylene-vinyl acetate (EVA) are produced via specific polymerization techniques and polymerization processes. Particle sizes are generally from 3 to <1 mm, and porosity can be above 50% by volume, and the products can therefore absorb suitably large amounts of unsaturated organosilane/mixtures, for example of the general formula III, and/or of the silicon-containing precursor compound, or a mixture of these, without losing their free-flow properties.

Particularly suitable waxes are polyolefin waxes based on low-density polyethylene (LDPE), preferably branched, with long side chains. The melting and freezing point is generally from 90 to 120° C. The waxes generally give good results in mixing with the unsaturated organosilanes, such as vinylalkoxysilane, and/or with the silicon-containing precursor compound, or a mixture of these, in a low-viscosity melt. The solidified mixture is generally sufficiently hard to be capable of granulation.

The various commercially available forms of carbon black are suitable by way of example for producing black cable sheathing.

The following methods inter alia are available for producing the compositions (dry liquids) on carriers, examples being compositions made of olefinic silane carboxylates, such as vinylsilane carboxylate of myristic acid or lauric acid, and carrier material, or else of vinylsilane stearate and carrier material, or of a tetracarboxysilane and vinylalkoxysilane with carrier material:

Among the best-known methods is spray drying. Alternative methods are explained in more detail below: mineral carriers or porous polymers are generally preheated, e.g. to 60° C. in an oven, and charged to a cylindrical container which has been flushed with, and filled with, dry nitrogen. A vinylalkoxysilane and/or vinylcarboxysilane is generally then added, and the container is placed in a roller apparatus which rotates it for about 30 minutes. After this time, the carrier substance and the liquid, high-viscosity or waxy alkoxysilane and/or carboxysilane have usually formed flowable, dry-surface granules which are advantageously stored under nitrogen in containers impermeable to light. As an alternative, the heated carrier substance can be charged to a mixer flushed and filled with dry nitrogen, e.g. a plowshare mixer of LÖDIGE type or a propeller mixer of HENSCHEL type. The mixer element can then be operated and the olefinic alkoxysilane and/or carboxysilane, in particular of the formula I, or a mixture of these, can be sprayed in by way of a nozzle once the maximum mixing rate has been reached. When addition has been completed, homogenization generally continues for a further approximately 30 minutes, and the product is then discharged into nitrogen-filled containers impermeable to light, for example by means of a pneumatic conveying system operated with dry nitrogen.

Polyethylene wax or any other wax in pelletized form with a melting point of from 90 to 120° C. or above can be melted in portions in a heatable vessel with stirrer, reflux condenser, and liquid-addition apparatus, and maintained in the molten state. Dry nitrogen is suitably passed through the apparatus during the entire production process. By way of the liquid-addition apparatus it is possible by way of example to add the liquid vinylcarboxysilane/mixtures progressively to the melt and mix these with the wax by vigorous stirring. The melt is then generally discharged into molds to solidify, and the solidified product is granulated. As an alternative, the melt can be allowed to drip onto a cooled molding belt on which it solidifies in the form of user-friendly pastilles.

The invention also provides a masterkit, in particular comprising a composition described above, where the masterkit comprises, as component A
- from 0.1 to 20% by weight, in particular from 0.1 to 10% by weight, preferably from 0.1 to 5% by weight, particularly preferably from 0.1 to 3% by weight, preferably from 0.5 to 5% by weight, in component A, of at least one silicon-containing precursor compound of an organic acid, in particular of the general formula I and/or II as defined above, or at least one organic acid, or one silicon-free precursor compound comprising an organic acid, in particular as defined above, and a carrier material making up 100% by weight of component A, or
- in alternatives, also a stabilizer, an added substance, or a mixture of these, making up 100% by weight of component A, and
- if appropriate, as component B, from 60 to 99.9% by weight, in component B, of an organofunctional silane compound of the formula III, where the definitions of b, a, B, R$^4$, and R$^5$ are as above, and also
- if appropriate from 0.05 to 10% by weight of a free-radical generator, and
- if appropriate from 0.05 to 10% by weight of at least one stabilizer, and/or
- from 0.05 to 99.99% by weight of at least one carrier material, stabilizer, added substance, or a mixture of these, where added substances that can be used comprise fillers and additives or a mixture of these, where the quantitative data give a total of 100% by weight in component B. Suitable added substances have been described above.

Particular carrier materials that can be used are those mentioned above, examples being PE, PP, and also others mentioned above. Similar considerations apply to the free-radical generator and to the stabilizer. Components A and B are preferably present separately from one another within the masterkit where the intention is to use them in two steps of the process. In the case of simultaneous use, the two components A and B can be present together in a physical mixture, for example in the form of powder, granules, or pellets, or else can be present in a single formulation, for example in pellet form or tablet form. A masterbatch of the invention comprises a vinyltriethoxysilane, for example vinyltrimethoxysilane, a peroxide, and also a processing aid, and also a silicon-containing precursor compound of an organic acid, if appropriate with a carrier material.

One preferred masterkit comprises by way of example 2% by weight of an organic acid, such as a fatty acid, in particular myristic acid, or lauric acid, on a polymeric carrier material, such as HDPE, where the amount of HDPE present is 98% by weight of the masterkit (component A), making up the balance of 100% by weight. Other masterkits comprise as organic acid preferably behenic acid, L-leucine, capric acid, oleic acid, lauric acid, and/or myristic acid, if appropriate in a mixture on a carrier material, for example HDPE.

The component B present can preferably comprise an unsaturated alkoxysilane, in particular of the formula III, or oligomeric siloxanes produced therefrom, preferably vinyltrimethoxysilane or vinyltriethoxysilane, together with a free-radical generator and with a stabilizer, if appropriate with further additives. Preferably on a carrier material, for example in the form of granules.

The invention also provides a process for producing compounded polymer materials, examples being granules, finished products, and moldings, in particular of unfilled or filled polymers, by 1) reacting a mixture made of thermoplastic parent polymer, in particular with a component of group a) at least one silicon-containing precursor compound of an organic acid and/or one organofunctional silane compound and, if appropriate, in particular with a component of group b) an organic acid, a silicon-free precursor compound containing an organic acid, and also a free-radical generator, in a compounding apparatus, in particular in the presence of moisture, or
2) reacting a mixture made of thermoplastic parent polymer, in a first step, with a) an organofunctional silane compound, and also a free-radical generator, in particular for producing silane-grafted polymer, and shaping the material, in a subsequent, in particular immediately subsequent, step, with addition of at least one silicon-containing precursor compound of an organic acid, one organic acid, and/or one silicon-free precursor compound containing an organic acid, and crosslinking the material with exposure to moisture, or
3) reacting a mixture made of thermoplastic parent polymer, in a first step, with a) at least one olefinic silicon-containing precursor compound of an organic acid, in particular of the general formulae I and/or II, where z=1, 2, or 3, and also with a free-radical generator, and shaping the material, in a subsequent step, with addition of at least one silicon-containing precursor compound of an organic acid, one silicon-free precursor compound containing an organic acid, and/or one organic acid, and crosslinking the material with exposure to moisture, or
4) reacting a mixture made of monomer and/or prepolymer of the thermoplastic parent polymers with a) an organofunctional silane compound, and also a free-radical generator, in particular for producing silane-copolymerized parent polymer, and shaping the material, in a subsequent, in particular immediately subsequent or nearly subsequent, step, with addition of at least one silicon-containing precursor compound of an organic acid, one organic acid, and/or one silicon-free precursor compound containing an organic acid, and then crosslinking the material with exposure to moisture.

In an alternative process of the invention for producing compounded polymer materials, such as granules, finished products, moldings, and in particular unfilled or filled polymers, 1) a mixture made of thermoplastic parent polymer is reacted with component B of the masterkit and component A of the masterkit described above in a compounding apparatus, and if appropriate is shaped at a given juncture, and crosslinked by moisture, or
2) a mixture made of thermoplastic parent polymer is reacted, in a first step, with component B of the masterkit described above and, in a subsequent step, is shaped, with addition of component A of a masterkit described above, and is crosslinked with exposure to moisture, or
3) a mixture made of monomer and/or prepolymer of the thermoplastic parent polymers is reacted with component B of the masterkit, as described in the introduction, and is shaped, in a subsequent step, with addition of component A of the masterkit, and is then crosslinked with exposure to moisture, and in particular a thermoplastic parent polymer is mixed with component B of the masterkit and reacted, and then granulated and, if appropriate, drawn off or packed by way of example in the form of PEg (PE granules) in an aluminum-coated sack. In a subsequent step, component A is added to the granules (PEg), and mixed, and if appropriate shaped, and during this process or subsequently crosslinked in the presence of moisture; or
4) a mixture made of thermoplastic parent polymer is reacted with the composition described above or with a masterkit described above in a monosil process, in particular one of the abovementioned preferred compositions, or
5) a mixture made of thermoplastic parent polymer is reacted with the composition described above, or with a masterkit described above, in a sioplas process, or
6) a mixture made of monomer and/or prepolymer of the thermoplastic parent polymers is reacted with a composition described above or with a masterkit described above, in a copolymerization process.

The invention also provides the reaction of a polymer kit, in particular as in Embodiment 15, in a monosil process or sioplas process, or in a copolymerization process.

One embodiment of the invention uses the composition described above, in particular as in Embodiments 1 to 8, and/or the masterkit, or the polymer kit, in the production of silane-grafted, silane-copolymerized, and/or crosslinked, in particular siloxane-crosslinked, filled or unfilled polymers.

The invention also provides the use of the composition or of the masterkit, or of the polymer kit, in particular in a monosil, sioplas, or copolymerization process, for producing filled and/or unfilled compounded polymer materials, which can take crosslinked or uncrosslinked form, and/or of crosslinked filled and/or unfilled polymers based on thermoplastic parent polymers. For the purposes of the invention, crosslinking in particular means the formation of an Si—O-substrate bond or Si—O-filler or Si—O-carrier material, or Si—O—Si bridging, i.e. the condensation of an Si—OH group with a condensable other group of a substrate.

Preference is given to the use for the production of silane-grafted, silane-copolymerized, and/or crosslinked, in particular siloxane-crosslinked, filled or unfilled polymers. The abovementioned polymers can also comprise block copolymers. It is preferable that the fillers are likewise crosslinked with the silicon-containing compounds, in particular by way of an Si—O-filler/carrier material bond. Particular fillers that can be used are the abovementioned fillers or carrier materials. In some of the abovementioned processes, it is preferable to use the unsaturated fatty acids. There are therefore sometimes no conventional organic acids used, examples being acetic acid, formic acid, maleic acid, maleic anhydride, or stearic acid.

The process as claimed in Embodiment 10 paragraph 1) is preferably conducted with at least one monounsaturated alkoxysilane corresponding to the formula III or one silicon-containing precursor compound of an organic acid, in particular of the formulae I and/or III, or with a mixture of the abovementioned compounds.

Preferred silicon-containing precursor compounds of the general formulae I and/or II are compounds where $R^1$ is a carbonyl-$R^3$ group selected from the group of the natural saturated and unsaturated fatty acids, in particular having hydrophobic hydrocarbon moieties having from 4 to 45 carbon atoms, in particular having from 6 to 45 carbon atoms, in particular having from 6 to 22 carbon atoms, preferably having from 8 to 22 carbon atoms, particularly preferably having from 6 to 14 carbon atoms, with particular preference where $R^3$ is from 11 to 13 carbon atoms, particularly preferably where z is 0 or 1. It can be preferable to use, in compositions, a monounsaturated alkoxysilane together with a compound of the formula I and/or II, where z is 0, 1, 2, or 3.

Preferred organic acids used for the thermoplastic parent polymers, or the silane-grafted and/or silane-copolymerized parent polymers, but in particular not for polyvinyl chlorides, are fatty acids selected from the group of the natural saturated and mono- or polyunsaturated fatty acids, in particular having hydrophobic hydrocarbon moieties having from 4 to 45 carbon atoms, in particular having from 6 to 45 carbon atoms in $R^3$, in particular having from 6 to 22 carbon atoms, preferably having from 8 to 22 carbon atoms, particularly preferably having from 6 to 14 carbon atoms, with particular preference where $R^3$ is from 11 to 13 carbon atoms, particularly preferably myristic acid and/or lauric acid. It can be preferable, in particular in a single-step process, to use, either alone or in compositions, a mono- or polyunsaturated alkoxysilane where a is 0, with no other alkylsilane.

The moisture-crosslinked unfilled or filled compounded polymer materials of the invention are generally produced via appropriate mixing of the respective starting-material components in the melt, as explained above for the processes, advantageously with exclusion of moisture. The usual heatable homogenization apparatuses are generally suitable for this purpose, examples being kneaders or advantageously for continuous operation Buss cokneaders or twin-screw extruders. As an alternative to these, it is also possible to use a single-screw extruder. A possible method here introduces the components continuously, in each case individually or in partial mixtures, in the prescribed quantitative proportion, to the extruder, which has been heated to a temperature above the melting point of the thermoplastic parent polymer. It is advantageous that the temperature rises in the direction toward the end of the screw, in order to establish a low viscosity and thus permit intensive mixing. In an advantageous method, the extrudates are still liquid when they are introduced to an apparatus for the molding of granules or of moldings, such as pipes. The final crosslinking of the unfilled or filled polymer generally takes place in a known manner in a waterbath, in a steam bath, or else via atmospheric moisture at ambient temperatures (the process known as "ambient curing").

At least one stabilizer and/or at least one further added substance, corresponding to the statements above, can be added in the process of the invention, prior to and/or during the process, and/or during one step of the process.

The invention also provides a polymer, for example a crosslinked filled or crosslinked unfilled polymer; a compounded polymer material, such as a compounded cable material, or a flame-retardant cable, for example filled with $Mg(OH)_2$ or $Al(OH)_3$, or with exfoliating materials, such as phyllosilicates; a filled plastic, an unfilled plastic and/or a molding and/or article obtainable by the process of the invention, in particular as in any of Embodiments 10 to 12. Appropriate moldings and/or items are cables, pipes, such as drinking-water lines, or products which can be used in the food-and-drinks sector or in the sector of hygiene products, or in the sector of medical technology, for example as medical instrument or part of a medical instrument, Braunüle, trocar, stent, clot retriever, vascular prosthesis, or component of a catheter, to mention just a few possibilities.

The invention further provides a polymer kit comprising the composition described above, in particular the components of group a), b), c), and/or d), and also, in particular separately from these, in the form of further component, component e) a thermoplastic parent polymer, an example being a silane-grafted parent polymer or silane-copolymerized parent polymer, or a monomer or prepolymer of the parent polymer, and/or a mixture of these. Components of group a), b), c), and/or d) can respectively be separated or, supported on a carrier in the polymer kit, can take the form of a mixture on fillers or on mineral carrier materials, for example on the abovementioned carrier materials, or else on carbon, an example being activated charcoal or carbon black.

An alternative polymer kit comprises the masterkit described above and also, as further component, a thermoplastic parent polymer, an example being a silane-grafted parent polymer or silane-copolymerized parent polymer, or a monomer or prepolymer of the parent polymer, and/or a mixture of these.

An example of a polymer kit is: 63.5% by weight of HDPE, 1.5% by weight of myristic acid, 5% by weight of Irganox 1010 (methyl 3-(3,5-di-tert-butyl-4-hydroxy-phenyl)propionate), and 30% by weight of Printex alpha pigment.

In the case of single-stage processes, for example in the case of the monosil process, the polymer and the composition that initiates crosslinking, the masterkit, or, in an alternative, the polymer kit only, are charged to the extruder, and the resultant melt is processed in one step to give the final product. The inventive composition used is appropriately a composition which comprises an organofunctional silane compound, in particular of the formula III, and which comprises a free-radical generator, and which also comprises a silicon-containing precursor compound of an organic acid or comprises an organic acid, and also, if appropriate, comprises a stabilizer.

For the production of filled plastics, the inorganic filler is mostly introduced directly to the compounding assembly and processed with the polymer to give the final product. The filler can also optionally be introduced at a later juncture into the assembly, for example in the case of a twin-screw extruder or cokneader. The graft polymer produced using the inventive composition or the inventive masterkit can give markedly better compatibility of nonpolar polymer and polar filler, for example aluminum hydroxide or magnesium hydroxide.

It is also possible to produce a graft polymer, in particular sioplas material, separately and, if appropriate, to granulate and package the material, in particular with protection from moisture, and to store the same and then to supply the same as feedstock to a processor, for example a cable producer or pipe producer, who in turn incorporates fillers to produce final filled plastics products.

The following examples provide further illustration of the inventive compositions, the masterkit, the polymer kit, and the inventive processes, but the invention is not restricted to these examples.

A) Production of alkyl- or alkenyltricarboxysilane, or tetracarboxysilane

GENERAL EXAMPLES a) For the production of alkenyltricarboxysilane, 1 mol of an alkenyltrichlorosilane, or in general terms an alkenyltrihalosilane, is reacted directly with 3 mol, or with an excess, of the organic monocarboxylic acid, or reacted in an inert solvent, in particular at elevated temperature.
b) For the production of an alkyltricarboxysilane, 1 mol of an alkyltrichlorosilane is correspondingly reacted directly with 3 mol, or with an excess, of an organic monocarboxylic acid, or is reacted in an inert solvent. It is preferable that the reaction takes place at elevated temperature, for example at up to the boiling point of the solvent, or at around the melting point of the organic fatty acid or of the organic acid.
c) For the production of tetracarboxysilanes, 1 mol of tetrahalosilane, in particular tetrachlorosilane or tetrabromosilane, is reacted with 4 mol, or with an excess, of at least one monocarboxylic acid, for example one fatty acid or fatty acid mixture. The reaction can take place directly via melting or in an inert solvent, preferably at elevated temperature.

Example 1

Production of vinyltristearylsilane

Reaction of 1 mol of vinyltrichlorosilane with 3 mol of stearic acid in toluene as solvent: 50 g of stearic acid (50.1 g) were used as initial charge with 150.0 g of toluene in a flask. The solid dissolves after gentle heating. Cooling gives a cloudy, highly viscous mass, which when reheated again forms a clear liquid. The oil bath was set to 95° C. at the start of the experiment, and about 20 minutes of mixing time gave a clear liquid. 9.01 g of vinyltrichlorosilane were then rapidly added dropwise with a pipette. After about 10 min the mixture was a clear liquid, and the oil temperature was adjusted to 150° C. After about a further 3 h after the start of the experiment, the mixture was cooled under inert gas. It was worked up by distillative removal of the toluene. This gave a white solid which when melted had an oily and yellowish appearance. For further purification, the solid can be subjected to further rotary evaporator treatment, for example for a prolonged period (3-5 h) at an oil bath temperature of about 90° C. and at a vacuum <1 mbar. The solid was characterized as vinyltrichlorosilane by way of NMR ($^1$H, $^{13}$C, $^{29}$Si).

Example 2

Production of vinyltridecanoic acid

Reaction of 1 mol of vinyltrichlorosilane with 3 mol of capric acid in toluene as solvent: 60.0 g of capric acid (decanoic acid) were used as initial charge with 143.6 g of toluene in a flask. The oil bath was set to 80° C. at the start of the experiment, and the vinyltrichlorosilane was slowly added dropwise (about 0.5 h for 19.1 g) while the temperature of the mixture was about 55° C. After about 45 min, the temperature of the oil was increased to 150° C. After a reaction time of about a further 2 h, the oil bath was switched off, but the stirring, the water-cooling, and the nitrogen blanketing were continued until cooling was complete. The clear liquid was transferred to a single-necked flask, and the toluene was drawn off in a rotary evaporator. The oil bath temperature was set to about 80° C. The vacuum was adjusted stepwise to <1 mbar. The product was a clear liquid. The liquid was characterized as vinyltricaprylsilane by way of NMR ($^1$H, $^{13}$C, $^{29}$Si).

Example 3

Production of hexadecyltricaprylsilane

Reaction of 1 mol of Dynasylan® 9016 (hexadecyltrichlorosilane) with 3 mol of capric acid in toluene as solvent: 73.1 g of capric acid (decanoic acid) were used as initial charge with 156.2 g of toluene in a flask. The oil bath was set to 95° C. at the start of the experiment, and 50.8 g of Dynasylan® 9016 were added dropwise over a period of about 25 minutes. After about 30 min, the temperature of the oil was increased to 150° C. The experiment was terminated after reflux for about 1.5 h. The toluene was drawn off from the clear liquid in a rotary evaporator. The oil bath temperature was set to about 80° C. The vacuum was adjusted stepwise to <1 mbar. The product was a yellow oily liquid with a slightly pungent odor. The liquid was characterized in essence as hexadecyltricaprylsilane by way of NMR ($^1$H, $^{13}$C, $^{29}$Si).

Example 4

Production of vinyltripalmitylsilane

Reaction of 1 mol of vinyltrichlorosilane with 3 mol of palmitic acid in toluene as solvent: 102.5 g of palmitic acid were used as initial charge with 157.0 g of toluene in a flask. The oil bath was set to 92° C. at the start of the experiment, and the 22.0 g of vinyltrichlorosilane were slowly added dropwise over a period of about 15 minutes. After about 70 min, the temperature of the oil was increased to 150° C. The mixture was heated at reflux for about 4 h, and then the toluene was removed by distillation. The oil bath temperature was adjusted to about 80° C., and the vacuum was adjusted stepwise to 2 mbar. Cooling of the product gave a white, remeltable solid. The solid was characterized as vinyltripalmitylsilane by way of NMR ($^1$H, $^{13}$C, $^{29}$Si).

Example 5

Production of chloropropyltripalmitylsilane

Reaction of 1 mol of CPTCS (chloropropyltrichlorosilane) with 3 mol of palmitic acid in toluene as solvent: 40.01 g of palmitic acid were used as initial charge in a three-necked flask, and the oil bath was heated. Once all of the palmitic acid had dissolved, 11.03 g of the CPTCS (99.89% purity (GC/TCD)) were added dropwise within a period of about 10 min. The temperature was finally increased to 130° C. After about 3.5 h no further gas activity was observed in an attached gas-washer bottle, and the synthesis was terminated. The toluene was removed in a rotary evaporator. At a subsequent juncture, the solid was remelted and stirred at an oil bath temperature of about 90° C. under a vacuum of <1 mbar. After about 4.5 h, no further gas bubbles were observed. The solid was characterized as chloropropyltripalmitylsilane by way of NMR ($^1$H, $^{13}$C, $^{29}$Si).

Example 6

Production of propyltrimyristylsilane

Reaction of 1 mol of PTCS (propyltrichlorosilane, 98.8% purity) with 3 mol of myristic acid in toluene as solvent. The reaction was analogous to that in the above examples. The reaction product was characterized as propyltrimyristylsilane.

Example 7

Production of vinyltrimyristylsilane

Reaction of Dynasylan® VTC with myristic acid: 40.5 g of myristic acid and 130 g of toluene are used as initial charge in the reaction flask, and mixed and heated to about 60° C. 9.5 g of Dynasylan® VTC are added dropwise within a period of 15 min by means of a dropping funnel. The temperature in the flask increases by about 10° C. during addition. After addition, stirring is continued for 15 minutes, and then the temperature of the oil bath is increased to 150° C. During the continued stirring, gas evolution (HCL gas) can be observed. Stirring was continued until no further gas evolution was observed (gas discharge valve), and stirring was continued for 3 h. After cooling of the mixture, unreacted Dynasylan® VTC and toluene were removed by distillation at about 80° C. at reduced pressure (0.5 mbar). The product remaining in the reaction flask is stored overnight in the flask with N$_2$ blanketing and then discharged without further work-up. The product subsequently solidifies. About 44.27 g of crude product were obtained.

Example 8

Production of propyltrimyristylsilane

Reaction of Dynasylan® PTCS with myristic acid: 40.5 g of myristic acid and 150 g of toluene are used as initial charge in the reaction flask, and mixed and heated to about 60° C. Dynasylan® PTCS is added dropwise within a period of 15 minutes by means of a dropping funnel. The temperature in the flask increases by about 10° C. during addition. After addition the temperature of the oil bath is increased to 150° C. and stirring is continued for 3 h. During the continued stirring, gas evolution, HCL gas, can be observed. Stirring was continued until no further gas evolution was observed at the gas discharge valve. After cooling of the mixture, unreacted Dynasylan® PTCS and toluene were removed by distillation at about 80° C. at reduced pressure (0.5 mbar). The product was stored under inert gas and solidified. About 44.0 g of crude product were obtained.

B) Crosslinking Examples:

Dynasylan® SILFIN 24 (vinyltrimethoxy (VTMO), peroxide, and processing aid)

Example 9

Grafting of Dynasylan® SILFIN 24 HDPE with Masterbatch

Grafting of 95% by weight of Dynasylan® SILFIN 24 HDPE with 5% by weight of masterbatch, and crosslinking at 80° C. in a waterbath. The masterbatch comprised 2% by weight of catalyst.

TABLE 1

Overview of starting materials and gel contents

| Catalyst | Gel [%] 0 h | Gel [%] 4 h at 80° C. Waterbath | Gel [%] 22 h at 80° C. Waterbath |
|---|---|---|---|
| Behenic acid | 17 | 36 | 53 |
| Tryptophan | 9 | 18 | 34 |
| L-phenylalanine | 16 | 26 | 39 |
| L-leucine | 1 | 30 | 46 |
| Blind value | 13 | 16 | 34 |
| Caprylic acid | 25 | 37 | 49 |
| Oleic acid | 22 | 42 | 52 |
| Capric acid | 23 | 36 | 44 |
| Stearic acid | 24 | 44 | 56 |
| Palmitic acid | 25 | 39 | 53 |
| Myristic acid | 23 | 37 | 49 |
| Lauric acid | 31 | 37 | 48 |

All of the fatty acids and amino acids tested accelerate a crosslinking reaction within the silane-modified polymer.

Example 10

Grafting of Dynasylan® SILFIN 24 HDPE with Masterbatch

As Example 9, only with 0.2% by weight catalyst content within the masterbatch.

TABLE 2

Overview of starting materials and gel contents

| Catalyst | Gel [%] 0 h | Gel [%] 4 h at 80° C. Waterbath | Gel [%] 22 h at 80° C. Waterbath |
|---|---|---|---|
| Blind value | 1.00 | 11 | 25.37 |
| Stearic acid | 34 | 54.08 | 62.35 |
| Palmitic acid | 29 | 48.60 | 62.43 |

Example 11

Grafting of Dynasilan® SILFIN 24 HDPE with Masterbatch

As Example 9, only with 0.5% by weight catalyst content within the masterbatch.

TABLE 3

Overview of starting materials and gel contents

| Catalyst | Gel [%] 0 h | Gel [%] 4 h at 80° C. Waterbath | Gel [%] 22 h at 80° C. Waterbath |
|---|---|---|---|
| Blind value | 1 | 11 | 25 |
| Capric acid | 39 | 60 | 60 |
| Caprylic acid | 39 | 60 | 61 |
| Myristic acid | 38 | 59 | 64 |
| Behenic acid | 37 | 58 | 64 |
| Stearic acid | 37 | 61 | 66 |
| Oleic acid | 49 | 62 | 65 |
| Palmitic acid | 48 | 63 | 66 |
| Tegokat 216 (DOTL) | 67 | 70 | 69 |

Example 12

Grafting of Dynasylan® SILFIN 24 HDPE with Masterbatch

As Example 9, only with 1.0% by weight catalyst content within the masterbatch.

TABLE 4

Overview of starting materials and gel contents

| Catalyst | Gel [%] 0 h | Gel [%] 4 h at 80° C. Waterbath | Gel [%] 22 h at 80° C. Waterbath |
| --- | --- | --- | --- |
| Blind value | 12.51 | 16.43 | 33.60 |
| Behenic acid | 16.64 | 35.71 | 52.97 |
| Stearic acid | 24.17 | 43.86 | 55.72 |
| Oleic acid | 22.38 | 41.78 | 52.37 |
| Palmitic acid | 24.78 | 38.82 | 53.19 |
| Myristic acid | 23.08 | 37.40 | 48.97 |
| Capric acid | 22.91 | 35.79 | 44.18 |
| Tegokat 216 (DOTL) | 44.12 | 61.37 | 65.79 |
| Caprylic acid | 24.87 | 37.40 | 49.26 |

Example 13

Grafting of Dynasylan® SILFIN 24 HPDE with Masterbatch

Silane-grafted HDPE is reacted with various amounts of added myristic acid.

TABLE 5

Overview of starting materials and gel contents, 1.2 phr of Dynasylan® SILFIN 24

| Catalyst | Gel [%] 0 h | Gel [%] 4 h at 80° C. Waterbath | Gel [%] 22 h at 80° C. Waterbath |
| --- | --- | --- | --- |
| Blind value | 0 | 0 | 26 |
| 0.2% by weight of myristic acid | 29 | 60 | 70 |
| 0.075% by weight of DOTL | 40 | 70 | 73 |
| 0.5% by weight of myristic acid | 33 | 68 | 75 |
| 1.0% by weight of myristic acid | 47 | 72 | 76 |

Example 14

Grafting of Dynasylan® SILFIN 24 HPDE with Masterbatch

Silane-grafted HDPE is reacted with various amounts of added myristic acid.

TABLE 6

Overview of starting materials and gel contents, 1.4 phr of Dynasylan® SILFIN 24

| Catalyst | Gel [%] 0 h | Gel [%] 4 h at 80° C. Waterbath | Gel [%] 22 h at 80° C. Waterbath |
| --- | --- | --- | --- |
| Blind value | −0.37 | 0.73 | 29.72 |
| 0.2% by weight of myristic acid | 21.46 | 58.79 | 70.39 |
| 0.075% by weight of DOTL | 38.97 | 70.97 | 75.19 |
| 0.5% by weight of myristic acid | 21.46 | 58.79 | 70.39 |
| 1.0% by weight of myristic acid | 37.69 | 70.16 | 76.02 |

Example 15

Grafting of Dynasylan® SILFIN 24 HDPE with Masterbatch

Silane-grafted HDPE is reacted with various amounts of added myristic acid.

TABLE 7

Overview of starting materials and gel contents, 1.6 phr of Dynasylan® SILFIN 24

| Catalyst | Gel [%] 0 h | Gel [%] 4 h at 80° C. Waterbath | Gel [%] 22 h at 80° C. Waterbath |
| --- | --- | --- | --- |
| Blind value | 0 | 2 | 35 |
| 0.2% by weight of myristic acid | 27 | 65 | 73 |
| 0.075% by weight of DOTL | 44 | 73 | 78 |
| 0.5% by weight of myristic acid | 36 | 71 | 76 |
| 1.0% by weight of myristic acid | 56 | 77 | 78 |

The above experiments provide evidence that myristic acid achieves gel contents comparable to those achieved with DOTL. When myristic acid is used, the amount of exudation observed on the crosslinked products is zero to small, even at high concentrations.

The following catalyst was used for the above Examples to 15: 0.2, 0.5, and 1.0% by weight of catalyst content (myristic acid) and 0.075% by weight of DOTL (standard masterbatch), compared with a blind value. Grafted HDPE was produced here with 1.2; 1.4, and 1.6 phr of Dynasylan® SILFIN 24. In each case, the silane-grafted PE was mixed with 5% by weight of the catalyst masterbatch, and processed in the kneader. A HAAKE laboratory kneader was used for processing, and plaques were then compression-molded at 200° C. and crosslinked at 80° C. in the waterbath.

Processing Parameters:

Kneader, feed hopper, belt mold, belt take-off; filled feed zone,

Rotation rate: 30 rpm, temperature profile: 140° C./3 min; 2 min at 210° C.; 210° C./5 min Crosslinking time: 0 h, 4 h and 22 h

Example 16

Step A—Grafting of MG9641S HDPE from Borealis with Dynasylan® SILFIN 24 Mixtures The grafting took place in a (ZE 25) twin-screw extruder from Berstorff. The experiments produced strands. The crosslinking agent preparation was in each case applied for 1 h to the PE in a mixing drum, after predrying at 70° C. for about 1 h. The grafted strands were granulated after extrusion. The granules were packaged directly after the granulation process in bags coated with an aluminum layer and these were closed by welding. Prior to the welding process, the granules were blanketed with nitrogen.

Processing Parameters for the Grafting Reaction in the ZE 25

Temperature profile: −/150/160/200/200/210/210/210° C.

Rotation rate: about 100 rpm, addition: 1.5 phr of Dynasylan® SILFIN 24

Step B—Processing for the Crosslinking Study

The silane-grafted polyethylene was kneaded in a laboratory kneader (Thermo HAAKE, 70 cm$^3$) with the respective catalyst (temperature profile: 140° C./3 min; 2 min up to 210° C.; 210° C./5 min, kneader rotation rate: 30 rpm). The mixture was then pressed at 200° C. to give sheets. Crosslinking took place in a waterbath at 80° C. (4 h). The gel contents of the crosslinked sheets were determined (8 h, p-xylene, Soxhlet extraction).

1) Screening with Various Fatty Acids as Catalyst at 0.5% by Weight Concentration in Comparison with Tin Catalyst

TABLE 8

Gel contents for the study with various fatty acids as catalyst in comparison with tin catalyst

| Catalyst | Gel [%], 4 h at 80° C. Waterbath | Comments |
|---|---|---|
| No catalyst | 11 | |
| Caprylic acid | 60 | strong, pungent odor |
| Myristic acid | 59 | |
| Stearic acid | 61 | waxy exudation on surface of specimen |
| Palmitic acid | 63 | waxy exudation on surface of specimen |
| Dioctyltin dilaurate | 70 | |

2) Screening with Fatty Acids, Precursor Compounds of the Fatty Acids, and Amino Acids In each case 95% by weight of silane-grafted PE with 5% by weight of catalyst masterbatch, where the catalyst masterbatch comprised 98% by weight of HDPE and 2% by weight of catalyst (organic acid). The results can be found in table 9.

TABLE 1

Gel contents for the study with various catalysts

| Catalyst | Gel [%] 22 h at 80° C. Waterbath | Catalyst type |
|---|---|---|
| No catalyst | 34 | — |
| Magnesium stearate | 37 | Organic-acid-containing, silicon-free precursor compound of the fatty acid |
| L-leucine | 46 | Amino acid |
| Hexadecyltripalmitic acid silane | 49 | Silicon-containing precursor compound of a fatty acid |
| Behenic acid | 53 | Fatty acid |
| Tegokat 216 (DOTL) | 66 | Tin catalyst |

Example 17 a) Grafting of MG9641S HDPE from Borealis with Dynasylan® SILFIN 24

The grafting took place in a ZE 25 extruder from Berstorff. The crosslinking agent preparation was in each case applied for 1 h to the PE in a mixing drum, after predrying at 70° C. for about 1 h. The grafted strands were granulated after extrusion. The granules were packaged directly after the granulation process in polyethylene-aluminum-polyethylene packaging and these were closed by welding. Prior to the welding process, the granules were blanketed with nitrogen.

Processing Parameters for the Grafting Reaction in the ZE 25

Temperature profile: −/150/160/200/200/210/210/210° C.
Rotation rate: about 100 rpm,
Addition: 1.5 phr of Dynasylan® SILFIN 24 (CS/V039/08)

b) Kneading Processes

For the production of the masterbatch, 49.0 g of PE were kneaded in a HAAKE laboratory kneader with 1.0 g of catalyst, organic acid, or silicon-containing precursor compound.

Processing Parameters:
Kneader, feed hopper, tape die, tape take-off; filled feed zone,
Rotation rate: 30 rpm,
Temperature profile: 200° C./5 min c) Production of Mixture Made of 95% by Weight of Silfin 24 HDPE with 5% by Weight of Masterbatch A mixture made of 95% by weight of Silfin 24 HDPE with 5% by weight of the masterbatch comprising the catalyst is produced. Processing took place in a HAAKE laboratory kneader. A mixture made of 95% by weight of Silfin 24 HDPE mixture with 5% by weight of masterbatch is kneaded, then pressed at 200° C. to give sheets, and finally crosslinked in a waterbath at 80° C.

Processing Parameters:
Kneader, feed hopper, tape die, tape take-off; filled feed zone,
Rotation rate: 30 rpm,
Temperature profile: 140° C./3 min; 2 min up to 210° C.; 210° C./5 min
Crosslinking time: 0 h, 4 h, and 22 h Example 18

Crosslinking of Silane-grafted HDPE

Polyethylene was modified chemically (grafted, rotation rate: 30 rpm, temperature profile: 3 min at 140° C., 2 min from 140° C. to 200° C., 10 min 200° C.) with various vinylsilanes with addition of peroxide in a HAAKE data-gathering kneader. Once the graft reaction had been concluded, aluminum trihydroxide (ATH) was added to the kneader as water donor. The presence of postcrosslinking detectable by way of a marked increase in torque was checked. The following mixtures were used:

TABLE 10

Experimental mixtures

| | Dynasylan® VTMO | Vinyltripalmitic acid silane | Vinyltricapric acid silane |
|---|---|---|---|
| BCUP (tert-butyl cumyl peroxide) | ~0.1 g | ~0.14 g | ~0.1 |

TABLE 10-continued

Experimental mixtures

|  | Dynasylan® VTMO | Vinyltripalmitic acid silane | Vinyltricapric acid silane |
|---|---|---|---|
| Silane-containing compound | ~0.55 g | ~1.1 g | ~1.3 |
| HDPE | | 50 g | |
| ATH | | 2 g | |

Both experiments using vinyltricarboxysilanes revealed a marked increase in torque after addition of the ATH. The increase was considerably more marked than with vinyltrimethoxysilane. The conclusion from this is that the extent of crosslinking reaction is greater.

Example 19

Crosslinking of HDPE—Comparison of vinyltripalmitic acid silane with Dynasylan® SILFIN 06

For this study, the individual crosslinking preparations were admixed with the HDPE power and processed in the kneader (rotation rate: 35 rpm, temperature profile: 2 min at 150° C., in 3 min from 150 to 210° C., 5 min at 210° C.). Table 11 lists the formulations:

TABLE 11

Formulation

|  | Vinyltripalmitic acid silane |
|---|---|
| DCUP (dicumyl peroxide) | 0.025 g |
| Silane-containing compound | 1.5 g |
| HDPE | 50 g |

The kneaded specimen was pressed to give a sheet and then crosslinked at 80° C. in the waterbath. The gel content of the crosslinked specimens was measured after various storage times.

TABLE 12

Gel contents of crosslinked specimens

| Crosslinking time Waterbath, 80° C. | Gel content for vinyltripalmitic acid silane [%] |
|---|---|
| 0.5 h | 32 |
| 1 h | 32 |
| 2 h | 31 |
| 4 h | 33 |
| 24 h | 31 |

Example 20

Masterkit (Masterbatch)

The carboxysilanes produced were used as catalysts in the sioplas process. For this, 95% by weight of a polyethylene grafted with Dynasylan® SILFIN 24 were kneaded with 5% by weight of the catalyst concentrate (catMB) of the invention. First, a masterbatch was produced with 1 g of the respective catalyst and 49 g of HDPE in the kneader (temperature profile: 5 min at 200° C.). 2.5 g of this were then kneaded together with 47.5 g of the extruded Dynasylan® SILFIN 24 HDPE (temperature profile: 3 min at 140° C., from 140° C. to 210° C. in 2 min, 5 min at 210° C.), and then pressed at 200° C. to give sheets, and finally crosslinked at 80° C. in the waterbath. The catMB included respectively 2% by weight of the respective catalyst, in particular of the vinyltricarboxysilanes or fatty acids. The results were compared with a mixture without catalyst. The sheets were crosslinked at 80° C. in the waterbath. Table 13 shows the results of this crosslinking study.

TABLE 13

Overview of catalyst study in the sioplas process

| Catalyst/experiment number | Gel content [%] Uncrosslinked | Gel content [%] 4 h at 80° C. Waterbath | Gel content [%] 22 h at 80° C. Waterbath |
|---|---|---|---|
| Blind value - no cat. | 13 | 16 | 34 |
| Vinyltripalmitic acid silane | 17 | 33 | 46 |
| Hexadecyltripalmitic acid silane | 18 | 40 | 49 |
| Vinyltricapric acid silane | 23 | 36 | 46 |
| Hexadecyltricapric acid silane | 23 | 39 | 45 |
| Capric acid | 23 | 36 | 44 |
| Palmitic acid | 25 | 39 | 53 |

What is claimed is:
1. A masterkit, comprising:
(A) (a1) 0.1 to 10% of myristic acid, and
 (a2) from 90 to 99.9% of at least one of member selected from the group consisting of titanium dioxide, quartz, magnesium hydroxide, bentonite, montmorillonite, mica, talc, aluminum oxide hydroxides, boehmite, baryte, barium sulfate, lime, aluminates, aluminum silicates, and ZnO,
wherein (a1)+(a2) make up 100% by weight of (A), and
(B) (b1) 60 to 99.9% by weight of at least one organofunctional silane compound
selected from the group consisting of vinyltrimethoxysilane, vinyltriethoxysilane, vinylmethyldialkoxysilane, vinyltriethoxymethoxysilane, vinyltriisopropoxysilane, vinyltri-n-butoxysilane, 3-methacryloxypropyltriethoxysilane, 3-methacryloxypropyltrimethoxysilane, vinylethoxydimethoxysilane, and allylalkoxysilanes, and
(b2) 0.1 to 40% by weight of (B) of at least one member selected from the group consisting of a free-radical generator, stabilizer, carrier material and an added substance,
wherein (b1)+(b2) make up 100% by weight of (B).
2. The masterkit of claim 1, wherein (b2) comprises at least one member selected from the group consisting of the free-radical generator, stabilizer and carrier material.
3. The masterkit of claim 1, wherein (b2) comprises at least one carrier material.
4. The masterkit of claim 1, which is essentially anhydrous.
5. A polymer kit, comprising the master kit of claim 1 and separately therefrom at least one member selected from a thermoplastic parent polymer, a silane-grafted parent poly- mer, a silane-copolymerized parent polymer, a monomer, or prepolymer of the parent polymer.

6. A process for producing a compounded polymer material, comprising:
(1) reacting a mixture comprising a thermoplastic parent polymer with the masterkit of claim 1 in a compounding apparatus, and
(2) crosslinking the material from (1) by exposure to moisture.

7. A process for producing a compounded polymer material, comprising reacting a thermoplastic parent polymer with the masterkit of claim 1 in a monosil process.

8. A process for producing a compounded polymer material, comprising reacting a thermoplastic parent polymer with the masterkit of claim 1 in a sioplas process.

9. A process for producing a compounded polymer material, comprising reacting a monomer and/or prepolymer of a thermoplastic parent polymer with the masterkit of claim 1 in a copolymerization process.

10. A process for producing a compounded polymer material, comprising:
(1) reacting a thermoplastic parent polymer with (B) of the masterkit of claim 1, and
(2) shaping the material from (1) with addition of (A) of the masterkit of claims 1, and
(3) crosslinking the material from (2) by exposure to moisture.

11. A process for producing a compounded polymer material, comprising:
(1) reacting a monomer and/or prepolymer of a thermoplastic parent polymers with (B) of the masterkit of claim 1,
(2) shaping the material from (1) with addition of (A) of the masterkit of claims 1, and
(3) crosslinking the material from (2) by exposure to moisture.

12. A process for producing a compounded polymer material, comprising:
(1) reacting a mixture comprising a thermoplastic parent polymer with (a) at least one compound and (b) myristic acid, and a free-radical generator, in a compounding apparatus, or
(2) reacting a thermoplastic parent polymer, in a first step, with (a) an organofunctional silane compound, and also a free-radical generator, and shaping the material in a subsequent step, with addition of myristic acid, and crosslinking the shaped material with exposure to moisture, or
(3) reacting a thermoplastic parent polymer in a first step with (a) a free-radical generator, and shaping the material in a subsequent step, with addition of myristic acid, and crosslinking the shaped material with exposure to moisture, or
(4) reacting a monomer and/or prepolymer of a thermoplastic parent polymer with (a) an organofunctional silane compound, and also a free-radical generator, and shaping the material in a subsequent step, with addition of myristic acid, and then crosslinking the shaped material with exposure to moisture.

13. The masterkit of claim 1, wherein said at least one organofunctional silane compound is an allylalkoxysilane which is allyltriethoxysilane.

14. The polymer kit of claim 5, comprising a thermoplastic parent polymer selected from the group consisting of polyamides, polycarbonate, polyethylene, polypropylene, polystyrene, polyvinyl chloride, ethylene-vinyl acetate copolymers, EPDM, EPM and a mixture thereof.

* * * * *